United States Patent
Hayes

(10) Patent No.: US 8,315,447 B2
(45) Date of Patent: Nov. 20, 2012

(54) METHOD FOR PROCESSING MEDICAL IMAGE DATA AND MAGNETIC RESONANCE APPARATUS FOR RECORDING AND PROCESSING MEDICAL IMAGE DATA

(75) Inventor: Carmel Hayes, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 791 days.

(21) Appl. No.: 12/320,990

(22) Filed: Feb. 10, 2009

(65) Prior Publication Data

US 2009/0214090 A1 Aug. 27, 2009

(30) Foreign Application Priority Data

Feb. 12, 2008 (DE) .................... 10 2008 008 601

(51) Int. Cl.
- G06K 9/00 (2006.01)
- A61B 6/00 (2006.01)
- A61B 5/05 (2006.01)

(52) U.S. Cl. ........ 382/128; 382/130; 382/131; 382/133; 128/922; 378/4; 378/21; 600/425

(58) Field of Classification Search .......... 382/128–133; 128/922; 378/4–27; 600/425
See application file for complete search history.

(56) References Cited

U.S. PATENT DOCUMENTS

| | | | |
|---|---|---|---|
| 5,903,664 A | 5/1999 | Hartley et al. | |
| 6,961,454 B2 * | 11/2005 | Jolly | 382/131 |
| 7,277,565 B2 | 10/2007 | Rasche et al. | |
| 2003/0069494 A1 | 4/2003 | Jolly | |
| 2005/0238215 A1 | 10/2005 | Jolly et al. | |
| 2006/0203955 A1 | 9/2006 | Grass | |
| 2009/0003672 A1 * | 1/2009 | Maier et al. | 382/128 |
| 2009/0010505 A1 | 1/2009 | Cocosco et al. | |
| 2009/0190813 A1 * | 7/2009 | Qu et al. | 382/130 |

FOREIGN PATENT DOCUMENTS

| | | |
|---|---|---|
| DE | 19746936 A1 | 5/1998 |
| DE | 10129631 A1 | 1/2003 |
| EP | 1061474 A1 | 12/2000 |
| WO | WO 2006/103594 | 5/2006 |
| WO | 2006083588 A1 | 8/2006 |

OTHER PUBLICATIONS

Office Action for corresponding German application No. 10 2008 008 601.0-53 dated Aug. 26, 2009.
Andrew C. Larson et al. "Preliminary Investigation of Respiratory Self-Gating for Free-Breathing Segmented Cine MRI," Magnetic Resonance in Medicine, 53: 159-168 (2005).

(Continued)

*Primary Examiner* — Georgia Y Epps
*Assistant Examiner* — Magda Cruz
(74) *Attorney, Agent, or Firm* — Harness, Dickey & Pierce, P.L.C.

(57) ABSTRACT

A method is disclosed for processing medical image data which image a structure layer by layer, the image data for at least some layers respectively including a plurality of layer images. In at least one embodiment, the method includes segmentation of the structure in the layer images and determination respectively of a position of a point in a layer image. In at least one embodiment, at least one layer image set is furthermore compiled on the basis of the representative points in the layer images.

38 Claims, 10 Drawing Sheets

OTHER PUBLICATIONS

Automated segmentation of the left ventricle in cardiac MRI; Kaus, M.R. et al.; Medical Image Analysis 8 (2004) 245-254; Magazine.

Combining Edge, Region, and Shape Information to Segment the Left Ventricle in Cardiac MR Images; Jolly, M.- P.; Proc. Medical Image Computing and Computer-Assisted Intervention 2001, 482-490; Magazine.

Snakes, Shapes, and Gradient Vector Flow; Xu, C., Prince, J.L.; IEEE Transactions on Image Processing, vol. 7, No. 3, Mar. 1998; Magazine; 1998.

Left Ventricular Mass and Volume: Fast Calculation with Guide-Point Modeling on MR Images; Young, A.A. et al.; Radiology 2000, 216:597-602; Magazine; 2000.

Automatic heart localization from a 4D MRI dataset; Sörgel, W., Vaerman, V.; SPIE: Med. Imag. 1997 vol. 3034, 333-344; Magazine; 1997.

2D Cardiac Function during Free-breathing with Navigators; Peters, D.C. et al.; Proc. Int'l Society for Magnetic Resonance in Medicine, 2007, 3856; Magazine; 2007.

Timo Makela et al., A Review of Cardiac Image Registration Methods; IEEE Transactions on Medical Imaging, vol. 21, No. 9, Sep. 2002; Others; 2002.

C. Hayes et al: "Fully automatic segmentation of the left ventricle in cardiac cine MR images" Proc. International Society for Magnetic Resonance in Medicine, 2007, 3695: Magazine; 2007.

A.S. Pednekar et al.: "Automatic Identification of the Left Ventricle in Cardiac Cine-MR Images: Dual-Contract Cluster Analysis and Scout-Geometry Approaches", J. Magn Reson Imaging 2006, 23: 641-651; Magazine; 2006.

Andrew C.Larson et al. "Self-Gated Cardiac Cine MRI", Wiley-Liss, Magnetic Resonance in Medicine, vol. 51, pp. 93-102 (2004); Others.

Office Action for corresponding German Application No. 10 2008 008 601.0-53 dated May 19, 2009.

* cited by examiner

FIG 5
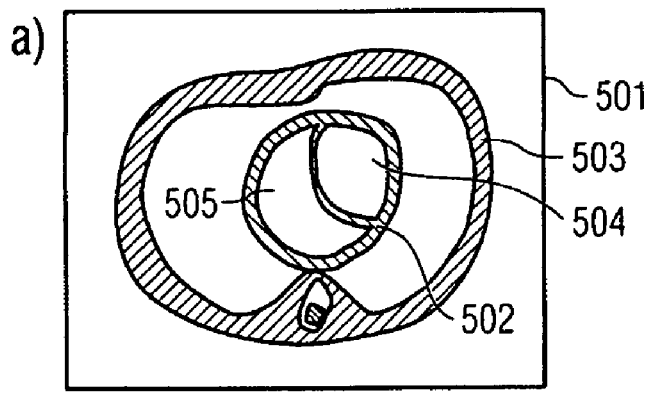
a)
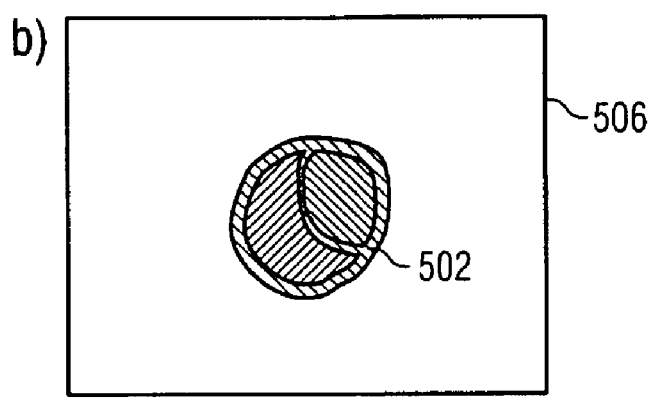
b)
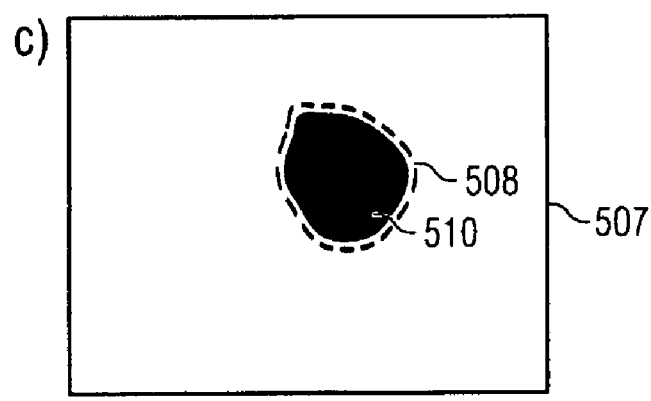
c)
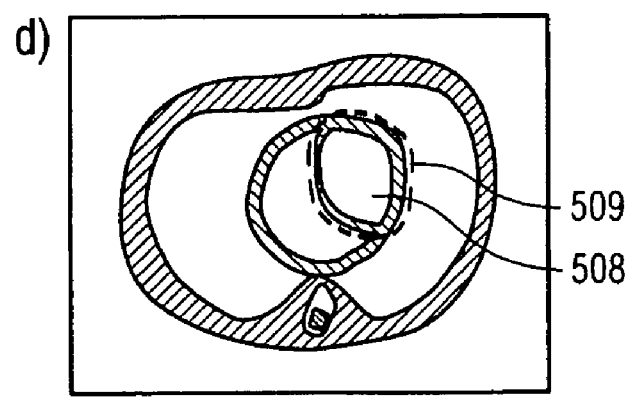
d)

METHOD FOR PROCESSING MEDICAL IMAGE DATA AND MAGNETIC RESONANCE APPARATUS FOR RECORDING AND PROCESSING MEDICAL IMAGE DATA

PRIORITY STATEMENT

The present application hereby claims priority under 35 U.S.C. §119 on German patent application number DE 10 2008 008 601.0 filed Feb. 12, 2008, the entire contents of which is hereby incorporated herein by reference.

FIELD

At least one embodiment of the present invention generally relates to a method for processing medical image data and/or to a magnetic resonance apparatus, with which medical image data can be recorded and processed.

BACKGROUND

In order to examine a subject's organs, it is often helpful to represent these organs by way of imaging. Magnetic resonance (MR) tomography is a suitable method for examining ventricles of the heart, and studies have shown that more reproducible and more accurate measurement of the volume and mass of a ventricle can be carried out with this imaging technique than with other imaging techniques. For MR imaging of the ventricular function, for example, two-dimensional images which show the movement of the heart at short time intervals (for example 40 ms) are recorded over a particular duration. These images can be recorded while the subject is holding his or her breath or while the subject is breathing freely.

The recording of magnetic resonance signals may furthermore be initiated by triggering, for example recording triggered by an electrocardiogram (ECG), or the magnetic resonance signals may be recorded without triggering. For evaluation of the image data reconstructed from the recorded magnetic resonance signals, it is necessary to segment the left ventricle in the image data.

There are a number of methods for segmenting the left heart valve in magnetic resonance images. The left ventricle may for example be segmented by a method which combines edges, regions and shape information (M. P. Jolly, "Combining Edge, Region and Shape Information to Segment the Left Ventricle in Cardiac MR Images", Proc. Medical Image Computing and Computer-Assisted Intervention, The Netherlands, 2001, 482-490). Another conventional method uses a finite element model, which represents the geometry of the left ventricle, and combines this with points which have been input by a user in order to obtain an estimate of the boundaries of the left ventricle (A. A. Young et al., "Left Ventricular Mass and Volume: Fast Calculation with Guide-Point Modeling on MR images", Radiology 2000; 216: 597-602). In M. Kaus et al., "Automated segmentation of the left ventricle in cardiac MRI", Medical Image Analysis, 2004; 8:245-254, a deformable shape model was used in order to carry out heart muscle segmentation fully automatically. The methods described above, however, have some essential disadvantages which will be described below.

Often, reliable examination of the ventricular function and in particular the evaluation of parameters, for example the volume, is made difficult by the fact that it is hard for a subject to hold their breath when a time series of layer images is being recorded. In order to overcome this problem, magnetic resonance images of the cardiac function may be recorded while the subject is breathing freely. Available methods for such recording are realtime imaging, breath triggering, self-triggering (for example based on MR image data) or "navigator gating", in which breathing-induced movement is determined and the image data are subsequently corrected for this. Realtime images are for example complete images which are recorded within a short duration, for example 60 ms.

Such imaging techniques are becoming ever more important for the examination of cardiovascular function, since they provide images with a quality which is sufficient for medical diagnosis, and these images of subjects can be recorded while they are breathing freely. Such techniques are advantageous particularly for patients who have difficulty in holding their breath. With conventional methods, it is not however possible for image data, recorded without breath triggering while the subject is breathing, to be segmented for quantitative analysis. The lack of suitable methods is essentially due to a lack of reliable image registering or processing tools with which different layers, recorded in various breathing positions, can be aligned. Conventional image registering methods are very computer-intensive and often lead to modification of the image data, for example by interpolation, which is likewise disadvantageous.

A conventional solution for overcoming this problem is so-called "navigator gating", in which so-called registering of image data is not in principle necessary (D. C. Peters et al., "2D Cardiac Function during Free-breathing with Navigators", Proc. International Society for Magnetic Resonance in Medicine 2007, 3860). With this technique, however, the times taken to record image data are substantially longer compared with the recording time for the same volume with realtime imaging (for example 10 minutes with navigator gating compared with 2 minutes for realtime recording).

SUMMARY

At least one embodiment of the present invention provides an improved method with which a structure can be segmented in image data which have been recorded from a freely breathing subject, as well as a magnetic resonance apparatus for carrying out the method.

In at least one embodiment of the invention, an improved method is disclosed for the quantitative processing of such image data.

A first aspect of an embodiment of the present invention provides a method for processing medical image data which image a structure layer by layer, the image data for at least some layers respectively comprising a plurality of layer images. The method comprises the following steps: automatic segmentation of the structure in the layer images; automatic determination respectively of a position of a point in a layer image, the point being representative of the structure segmented in the layer image, for a plurality of layer images in which the structure has been segmented; and automatic compilation of at least one layer image set by allocating a layer image to the layer image set respectively for a plurality of layers, the allocation being carried out on the basis of the positions of the representative points in the layer images.

Such a method makes it possible to generate a layer image set in which the structure is segmented, and which can therefore be used for further evaluation of for example functional parameters of the structure. For example, the image data respectively comprise the same number of layer images for a particular number of layers, and the structure is segmented in each of the layer images and a representative point is calculated, on the basis of which a layer image is subsequently selected from each layer in order to compile the layer image set. Such allocation of layer images is advantageous since, on the basis of the representative point, it is possible to select layer images from the various layers which for example fit together in relation to the breathing phase of the subject from which the image data have been recorded. For segmentation of the structure, for example, a segmentation region is calculated by calculating a contour around the structure in the respective layer image. The segmentation of the structure in a layer image is generally carried out in two dimensions since a layer image essentially represents a section through the structure, and may therefore also be referred to as a section image. With the aid of the two-dimensional segmentation regions of the layer image set, it is possible to calculate a three-dimensional segmentation volume.

Various points, which are representative of the segmented structure, may be envisaged. For example, the representative point in a layer image may be the centroid of the structure segmented in the layer image. For segmentation of the structure, for example, a segmentation region or a segmentation area may thus be calculated and the geometrical centroid of such a region or such an area may then be used as a representative point. Particularly for structures with special geometrical properties, it is advantageous to allocate the layer images to a layer image set on the basis of the segmented structure in the respective layer image since, even with layer images which have been recorded from a breathing subject, it is possible to obtain a layer image set in which consecutive layer images match one another in respect of the position of the structure. The method does not require any modification of the image data or elaborate and computer-intensive interpolations of the image data.

Compared with the otherwise conventional "image registering", for which one image is selected as a reference and the other images are "registered" to this image by modification, such modification of the image data is not necessary in the method described here. Image registering methods are suitable for rigid structures, for example for a subject's head, but they are not suitable for soft tissue and particularly when there is movement of the structure, for example in the case of a beating heart and with additional breathing. The method is particularly suitable for segmentation of a subject's left ventricle, since this has a geometrical shape in which the centroids in short-axial section images of the ventricle lie on an axis.

According to one embodiment of the present invention, the medical image data are recorded from a subject before or during processing, while the subject is breathing freely. The medical image data are preferably recorded using a magnetic resonance apparatus, for example by detecting magnetic resonance signals and subsequently reconstructing the image data from these signals. It is however also conceivable for the image data to be recorded using other imaging methods, for example computer tomography or ultrasound imaging methods, in which case it is preferable to employ methods which image the structure layer by layer. The processing of such image data with the method according to the invention is particularly advantageous, since the structure can be segmented in three dimensions in the image data even though the subject is breathing freely. Although the subject's free breathing leads to a displacement of the structure in the image data, this can be compensated for by compiling the layer image set on the basis of the representative points.

Each layer image may be allocated a time stamp, which indicates the recording time of the layer image relative to a preceding trigger event. The occurrence of the trigger event may for example be determined by using a vector cardiogram (VCG), an electrocardiogram (ECG) and/or a pulse trigger device. The image data in this case preferably comprise at least two time series of layer images for each layer, each time series having been recorded following a trigger event. It is particularly advantageous for the layer images of a time series to have a time interval of between 20 and 100 ms. A time interval of between 50 and 70 ms is particularly preferred.

It is also advantageous that the image data for each layer should comprise consecutive time series of layer images which extend over a duration of at least two breathing cycles of a subject from which the image data have been recorded. When recording a time series of layer images, the triggering preferably takes place on the R-wave peak of an ECG of the subject. The image data may thus be obtained, for example, by recording over a predetermined duration for each layer of a predetermined number of layers, or by recording a predetermined number of layer images for each trigger event of a predetermined number of trigger events. The allocation of time stamps relative to the trigger event will ensure that all layer images with the same time stamps image, for example, the same cycle of a heartbeat. In this example, a time series of layer images extends over one heartbeat, i.e. from one trigger event to the next.

Recording the layer images with a time interval of the order of 60 ms will in this case be considered as realtime recording. For a layer, layer images are for example recorded over 10 seconds, and the layer images may furthermore be allocated an absolute time stamp which indicates the time relative to the start of recording. Recording layer images from a layer over a duration of at least two breathing cycles then has the advantage that the image data comprise layer images which image the structure in different positions which are caused by the thoracic movement due to breathing. With image data which have been recorded in this way, it is generally possible to find an image data set which comprises layer images with essentially matching representative points.

A layer image set is preferably allocated only layer images which have an essentially equal time stamp. This will ensure that the layer image set comprises, for example, only layer images from the same phase of a cardiac cycle. At least one layer image set may in this case be compiled for each time stamp. The structure can therefore be segmented for various phases after the trigger event, which makes it possible to pick up any variation of the structure as a function of time.

Since a plurality of layer images are available for each layer and for each time stamp in the embodiment described here, it is also possible to compile more than one layer image set for each time stamp, for example from various phases of the breathing cycle. If the left ventricle is being imaged as a structure in the image data, then for example a volume change of the left ventricle in various phases of the cardiac cycle may be found from the layer image sets for each time stamp, in which the ventricle is segmented.

An aim in one embodiment of the invention is to obtain a chronological sequence of layer image sets, which correspond to a cardiac cycle. It is advantageous that only layer images from the same time series (or cardiac cycle) should be used for each layer, since these will be physiologically connected.

The layer image sets may be compiled by selecting a time series for each layer. The selection of the multiple time series may in turn be carried out on the basis of the representative points, in which case for example only the representative point of the first layer image of each time series is used for the selection. Chronologically successive layer image sets may then be formed respectively from a layer image of the time series selected for each layer. The allocation is preferably carried out on the basis of the time stamp.

The search for multiple time series in the various layers with the least possible spacings of the representative points may be carried out on the basis of the first image or one or more of the remaining images of the time series.

Such allocation of the images is possible, for example, because the displacement of the heart due to breathing is only small during a heartbeat.

The allocation of the layer images to the layer image sets may also take place during recording of the image data. For example, layer images of a layer are allocated to layer image sets while layer images of the layer following next are being recorded. One or more layer image sets are therefore already available at the end of recording the image data, and these may also be processed further in order to improve the allocation of layer images to the layer image sets with the aid of the representative points.

The structure may be segmented in a variety of ways in the image data. For example, a contour may be calculated around the structure in a layer image in order to establish a segmentation region. The segmentation of the structure in a layer image preferably comprises calculation of a contour around the structure by using an active contour method.

Various "active contour" methods are known to a person skilled in the art, for example "Snakes" or other gradient- or edge-based active contour methods which will not be discussed in further detail here. The calculation of a contour around the structure in the layer image may, for example, be carried out by placing marking points on the edge of the structure and calculating curve segments between these marking points. Automatic segmentation of the structure is, however, preferred. The segmentation may for example be carried out by using the method described in M. Kaus at al., "Automated segmentation of the left ventricle in cardiac MRI", Medical Image Analysis, 2004; 8:245-254, or in C. Xu and J. L. Prince, "Snakes, Shapes, and Gradient Vector Flow", IEEE Transactions on Image Processing, 1998; 7(3): 359-369, the entire contents of each of which are hereby incorporated herein by reference.

In one embodiment, the segmentation of the structure in a layer image comprises determination of an initial segmentation region of the structure in the layer image on the basis of variations of the structure in chronologically successive layer images. With the aid of chronologically successive layer images, a variance image may for example be compiled in which structures that experience variations as a function of time are predominantly contrasted. The determination of the initial segmentation region may comprise the use of a first threshold value for compiling a binary image with imaged structures based on a variance image.

The determination may furthermore comprise identification of the initial segmentation region on the basis of shape, connection and/or position of the imaged structures. A binary mask of the structure may also be calculated on the basis of a sum of variance images and a second threshold value. The determination of such a binary image, or a binary mask, is advantageous since this roughly indicates the position of the predominant moving structures in the layer images. In order to determine the initial segmentation region, a time series of images may for example be analyzed and the moving structures in a layer image may be identified by using image subtraction and statistical analysis.

For examination of other moving structures, for example of the left ventricle, it is possible to use properties of the structures which have been found in the binary image, for example shape properties such as roundness, connection of different structures, and position properties of the structures in the images. For the left ventricle, for example, it will be assumed that it constitutes a round object which lies in the vicinity of the image center. In each layer image, an initial segmentation region can therefore be established for the structure.

An initial segmentation region may also be established by the method which is described in W. Soergel and V. Vaerman, SPIE: Med. Imag. 1997; 3034; 333-344, the entire contents of which are hereby incorporated herein by reference. The rough position determination of the segmentation region may be carried out once for each time series of a layer, or only for one time series.

When the rough position of the segmentation region has been determined, an initial contour may be deformed in order to align it with the edges of the structure. An initial contour is preferably determined in a layer image on the basis of the initial segmentation region. In order to determine an initial contour, a method may be used as described in M. P. Jolly, "Combining Edge, Region and Shape Information to Segment the Left Ventricle in Cardiac MR Images", Proc. Medical Image Computing and Computer-Assisted Intervention, The Netherlands, 2001, 482-490, the entire contents of which are hereby incorporated herein by reference.

In order to establish the initial contour, for example, a model of the structure may be adapted to the initial segmentation region, in which case, when a three-dimensional model is available, a two-dimensional model for a layer image may be obtained by cutting the three-dimensional model with a plane. An already determined contour of a neighboring layer image, for example from a neighboring layer or from a preceding time, may also be used to determine the initial contour. The edge of the initial segmentation region may also be approximated simply with an ellipse or another geometrical shape.

For segmentation of the structure, the initial contour is preferably adapted to the edges of the structure in the layer image by using an active contour method. An initial contour is preferably deformed or adapted by using the method described in M. P. Jolly, Proc. MICCAI, 2001, the entire contents of which are hereby incorporated herein by reference. The local deformation process is carried out so that the contour is aligned with the edges of the structure in a layer image. The method described in this publication is preferably applied at least two times. This makes it possible to ensure that maximally accurate adaptation of the contour to the structure to be segmented takes place.

Such calculation of a contour around the structure in a layer image, or of a segmentation region, is particularly advantageous since this calculation can be carried out fully automatically. Determination of the initial segmentation region will avoid the disadvantages which may occur in methods of pure adaptation of contours to structures in layer images. Such methods cannot generally deal with the variable image intensities, which are encountered for example when imaging the heart. Here, therefore, rough position determination of the structure to be segmented is initially carried out in a layer image, on the basis of which an initial contour is determined which is subsequently adapted to the edges of the structure.

A consistency check of the shape and position of the calculated contours may furthermore be carried out. For example, the segmentation of the structure in the layer images comprises a check for differences in position and shape of contours in neighboring layer images of a time sequence, adaptation of the contours being carried out when it is found that the differences exceed a predetermined limit value. The method described in WO 2006/083588 A1, the entire contents of which are hereby incorporated herein by reference, is preferably used for adaptation of the contours. Owing to the threshold values and intensity variation, for example when imaging the heart, different initial segmentation regions may be determined for neighboring layer images.

Further calculation of the initial contours in order to adapt to the edges of the structure may subsequently give different contours in the neighboring layer images, and the discrepancies between the contours may be greater than the differences between the contours expected from the movement of the heart. In such a case, it is advantageous to correct the contour in order to ensure consistency between contours of chronologically neighboring layer images. A consistency check of contours may also be carried out over all layer images of a layer. The contours are compared in order to check consistency in position and shape of the contours and when necessary, for example when an inconsistency is found, propagation or adaptation of the contours may be carried out, for example by using the method described in WO 2006/083588 A1.

In another embodiment, the segmentation of the structure in the layer images of a layer may also be carried out by initially segmenting the structure in a first time series of layer images, for example by adapting an initially calculated contour to edges of the structure in the layer images. In a further time series of the same layer, the structure in the layer images may be segmented by adapting the contours of the first time series to the structure in the layer images of the second time series. This has the advantage that an initial segmentation region does not have to be determined for the second time series. The contours of the first time series are essentially used as initial contours, and are adapted to the contours of the structure in the layer images of the second time series. The computing power, which is required for segmentation of the structure, is therefore reduced and a time saving is achieved. However, the method is less suitable for cases in which the structure changes its position substantially between time series.

In general, the shape and position of the structure in each layer image are known after the segmentation. According to another embodiment of the invention, the position of a representative point in a layer image is determined on the basis of the shape and the position of the segmented structure in the layer image. The segmented structure is represented in a layer image for example by a segmentation region in the form of an area, in which case the geometrical centroid of the area may be determined as a representative point. It is however also conceivable to determine representative points other than the centroid, for example by weighting various regions of the segmented structure or by processing the image information of the segmented structure. The choice of the method, by which the representative point is calculated, is preferably dependent on the structure to be segmented, i.e. for example the shape of an organ to be segmented. Determination of the position on the basis of the shape and the position of the segmented structure is particularly advantageous, since suitable allocation of the layer images to the layer image sets can thereby be carried out, by which it is possible to ensure that the position of the structure varies only insubstantially between layer images of the layer image set.

According to one embodiment of the present invention, the allocation is carried out so that transverse spacings of the representative points of the layer images of a layer image set are minimized. Here, transverse spacings are spacings in the layer image plane. A layer image set preferably contains precisely one layer image for each layer, each layer image corresponding to a different axial position along an axis perpendicular to the plane of the layer images, which is defined for example as the z axis. The transverse direction and z axis mentioned here are not to be confused with the customary transverse direction and z axis in magnetic resonance tomography, where they indicate a direction respectively perpendicular or parallel to a $B_0$ field. Rather, the plane of the layer images referred to here may make a predetermined angle with the $B_0$ field. The coordinates in the plane of layer image may, for example, be denoted by x and y. A layer image set is then allocated layer images so that the spacings of the representative points in the layer image plane, i.e. x/y plane, are as small as possible. Preferably, the positions of the representative points of the layer images of a layer image set essentially coincide.

In another embodiment, at least two layer image sets are compiled and the layer images are allocated to the layer image sets so that transverse spacings of the representative points of the layer images in the individual layer image sets are minimized. A plurality of layer image sets may thus be compiled, and at least two layer image sets are preferably compiled respectively for various time stamps. The allocation is then carried out so that the representative points of the layer images in a layer image set lie as close as possible to one another in the transverse direction. As already mentioned, this allocation may be carried out during the recording of image data, for example by allocating recorded layer images of a layer directly to layer image sets. The allocation of a layer image to the layer image set may be carried out on the basis of the position of the representative point in the layer image and the position of the representative point in a layer image from a neighboring layer. Such allocation, which is based on layer images from neighboring layers, is advantageous when the allocation takes place during the recording of image data. However, displacements of the representative points within a layer image set may occur in the course of such allocation.

According to another embodiment, the allocation of layer images to a plurality of layer image sets may be carried out by an iterative sorting method, which allocates the layer images to the layer image sets so that the spacings of the representative points in each layer image set are minimized. Such a method may be used to process image data after recording the image data. It may, however, also be used to re-sort layer image sets which have been compiled by using representative points of neighboring layer images. Deviations of positions of representative points within a layer image set, which may occur because only positions of representative points of neighboring layer images are compared, can thus be corrected.

Alternative types of sorting the layer images, or compiling a layer image set, may also be envisaged. For example, the representative points of the layer images may also be aligned with the aid of an axis, for example a symmetry axis of a structure to be segmented. It is therefore possible to segment various structures by using the described method, on the basis of image data which have been recorded from a subject while he or she is breathing freely. The effect achieved by the allocation or sorting of the layer images is that the segmented structure lies essentially at the same position (transverse position) in layer images of a layer image set. A particular advantage of the method is that these layer image sets can be compiled automatically even though the position of the structure in the layer images varies, for example owing to breathing. Compared with the image registering method, here again no modification of the image data takes place, which on the one hand improves the quality and authenticity of the image data, and as a result of which on the other hand only a low computing power and a small time expenditure are required.

As an alternative, only one or more layer image sets may be compiled in the method and the remaining layer images, which have not been allocated to a layer image set, may be discarded. It is however also be possible to assign all recorded layer images to layer image sets. It is advantageous to compile fewer layer image sets than the number of layer images which have been recorded for a layer, since it is then possible to discard layer images in which the positions of the representative points do not coincide with those of the layer images already contained in the layer image sets. If the method is carried out in order to segment the left ventricle, then the centroids of the segmented ventricle of the layer images of a layer image set may for example lie along an axis from the opening of the mitral heart valve to the heart apex.

The method is advantageously refined by determining parameters, which relate to the function of the structure, on the basis of the structure segmented in the at least one layer image set. In an embodiment in which the structure is a subject's left ventricle, parameters which relate to the function of the left ventricle will be determined on the basis of the ventricle segmented in the at least one layer image set. For example the volume of the ventricle, the ejection fraction and/or the blood volume ejected by the ventricle may be determined on the basis of the ventricle segmented in the at least one layer image set. The use of layer image sets, which correspond to various phases or times in a cardiac cycle, is particularly advantageous for the calculation of functional parameters. Not only can mass and volume calculations of the left ventricle be carried out, but it is also possible to measure the wall movement of the ventricle. When employing the method according to the invention, not only can data sets of various phases of the cardiac cycle be obtained, but also layer image sets which correspond to the same phase of the cardiac cycle but different phases of the breathing cycle. Here again, it becomes possible to evaluate functional parameters which relate to the breathing activity.

For an evaluation, for example, an area of the segmented structure in a layer image or the volume of the segmented structure is calculated by using a Simpson method, a rectangle method or a numerical integration method. Such numerical methods for calculating an area or a volume of a segmented structure are known to the person skilled in the art and will therefore not be discussed in detail here. The use of such methods for area or volume calculation is advantageous since rapid and accurate calculation is ensured.

According to one embodiment of the invention, the volume of the structure is calculated for at least one layer image set by calculating, for each layer image, a layer volume of the segmented structure in the corresponding layer on the basis of a layer thickness and the area of the segmented structure in the layer image, and by adding the layer volumes of the segmented structure of the layer images of the layer image set. The height or layer thickness of a layer is generally known from the image data, and will in general be established during recording of magnetic resonance data. Calculation of the area of a segmentation region is possible by simple means, for example using one of the integration methods described above.

From the area of the segmentation region and the layer thickness, it is possible to calculate layer volumes of the individual layers of the layer image set, and summation over these layer volumes gives a volume of the segmented structure. Volumes of layer image sets with different time stamps, which have been calculated in this way, may then for example be used to calculate a volume change as a function of time. An evaluation of the layer image sets can thereby be carried out without great time expenditure.

It is, however, also possible to calculate a time-dependent volume from the layer images of the image data set in a different way. According to another aspect of an embodiment of the invention medical image data, which image a structure layer by layer, the image data for at least some layers respectively comprising a plurality of layer images, are processed by following steps: segmentation of the structure in the layer images in order to ascertain a segmentation region; determination of a layer volume of the structure for each of a plurality of layer images in which the structure has been segmented, on the basis of the respective segmentation region and a layer thickness; calculation of at least one average layer volume of the structure for each layer in which the structure has been segmented, by averaging layer volumes of layer images from the layer; and determination of at least one average volume of the structure by summing a layer volume of the structure respectively from each layer in which the structure has been segmented. The structure is preferably segmented in the layer images by using one of the methods described above.

Each layer image may furthermore be allocated a time stamp, which indicates the recording time of the layer image relative to a preceding trigger event. For each layer, a plurality of average layer volumes of the structure may be determined by respectively averaging the layer volumes, which are based on layer images from the layer with an equal time stamp, for different time stamps. Trigger events, which may be used to establish the time stamp, have already been described above. Here the same number of average layer volumes are preferably calculated for each layer, the average layer volumes of a layer having different time stamps. It is then possible to determine an average volume of the structure respectively for different time stamps, in which case the average volume for a time stamp may be determined by summing an average layer volume from each layer, which has been calculated for the corresponding time stamp. A time series of average volumes of the structure is therefore obtained.

The method of various embodiments may be carried out automatically, and it requires only a little time expenditure and only small computing power. The structure is preferably the left ventricle, in which case an ejection fraction or a blood volume ejected by the ventricle is determined from the average volumes of the left ventricle for different time stamps. The amount of blood ejected may, for example, be determined by comparing the minimum and maximum volumes of the time series of ventricular volumes. The steps of the method described above, in particular the steps which relate to the recording of image data, segmentation of the structure in layer images and evaluation of the structure segmented in the layer images, may be combined with the method described here and its embodiments, and vice versa.

Another aspect of an embodiment of the invention provides a magnetic resonance apparatus for recording and processing medical image data, having a recording unit for recording magnetic resonance data sets and a computer unit which, from a recorded magnetic resonance data set, reconstructs image data which image a structure layer by layer, the image data for at least some layers respectively comprising a plurality of layer images, the computer unit being configured so that it carries out the following steps: segmentation of the structure in the layer images; determination respectively of a position of a point in a layer image, the point being representative of the structure segmented in the layer image, for a plurality of layer images in which the structure has been segmented; and compilation of at least one layer image set by allocating a layer image to the layer image set respectively for a plurality of layers, the allocation being carried out on the basis of the positions of the representative points in the layer images.

The computer unit may also be provided in a computer system which is separate from the magnetic resonance apparatus and which is functionally connected to the magnetic resonance apparatus. The layer images may be processed by such a magnetic resonance apparatus during the recording of magnetic resonance data or after the end of recording the magnetic resonance data. A structure can be segmented into the image data by such a magnetic resonance apparatus without requiring the intervention of a user, and without the need to modify the image data. According to one embodiment, the magnetic resonance apparatus is furthermore configured for carrying out one of the methods described above.

A computer program product is furthermore provided in at least one embodiment, having a computer program which carries out one of the methods described above when it is run in a computer system. The computer program may for example contain program code segments which carry out one of the methods described above or parts of one of the methods described above.

An electronically readable data medium (computer readable medium) is furthermore provided in at least one embodiment, having, stored thereon, electronically readable control information which is configured so that it carries out one of the methods described above when the data medium is used in a computer system. Such a data medium may for example be used in a computer system of a magnetic resonance apparatus, so that one of the methods of at least one embodiment described above can be carried out by using such a magnetic resonance apparatus. The computer system may also be provided separately from a magnetic resonance apparatus, and be functionally connected to it.

The features of the aforementioned aspects and embodiments of the invention may be combined. In particular, they may be used not only in the described combinations, but also in other combinations or separately, without departing from the scope of the invention.

BRIEF DESCRIPTION OF THE DRAWINGS

Brief Description of the Drawings

The invention will be explained in more detail below with reference to example embodiments and the appended drawings.

Figure 1:
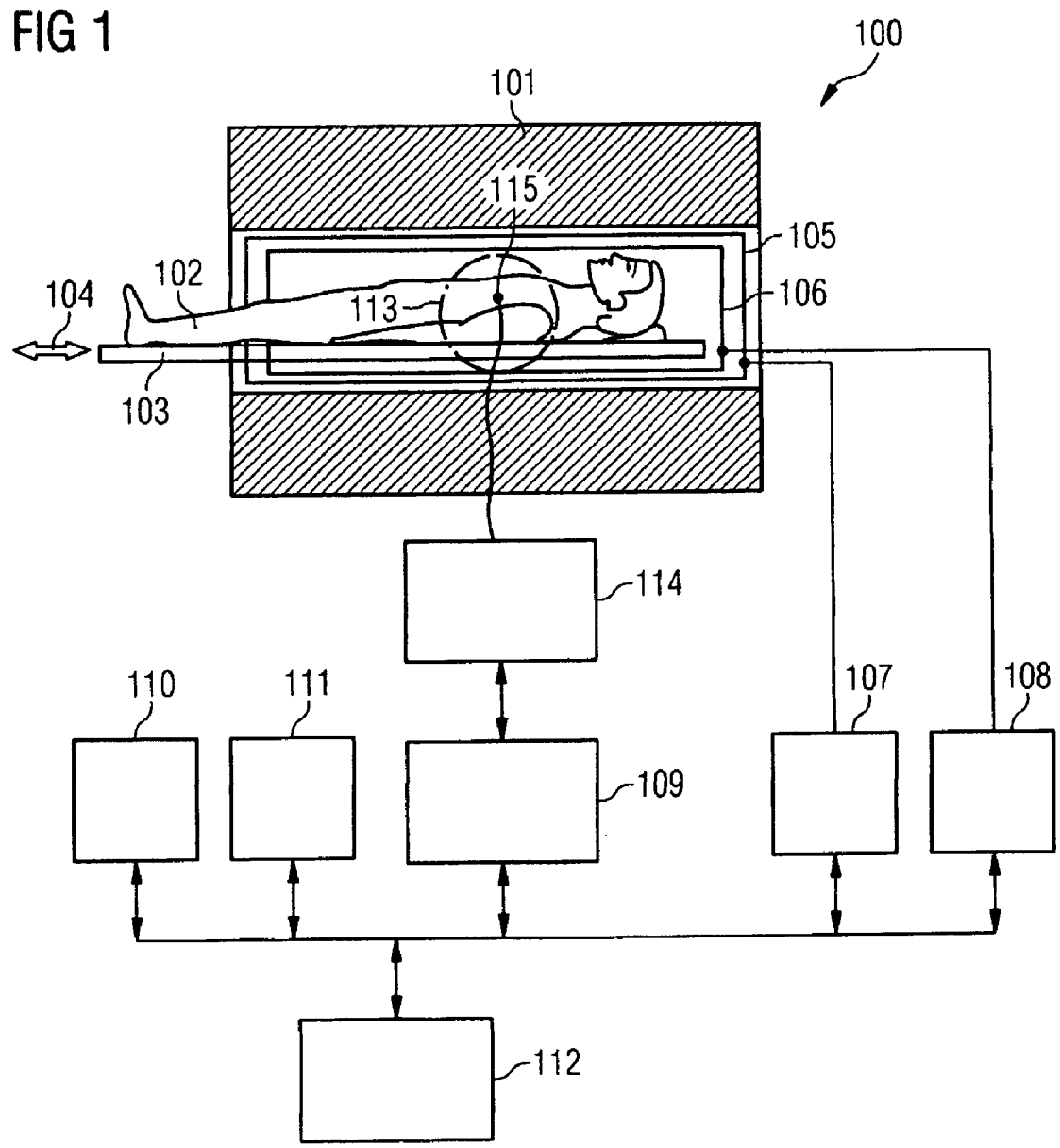

FIG. 1 shows a schematic representation of a magnetic resonance apparatus.

Figure 2:
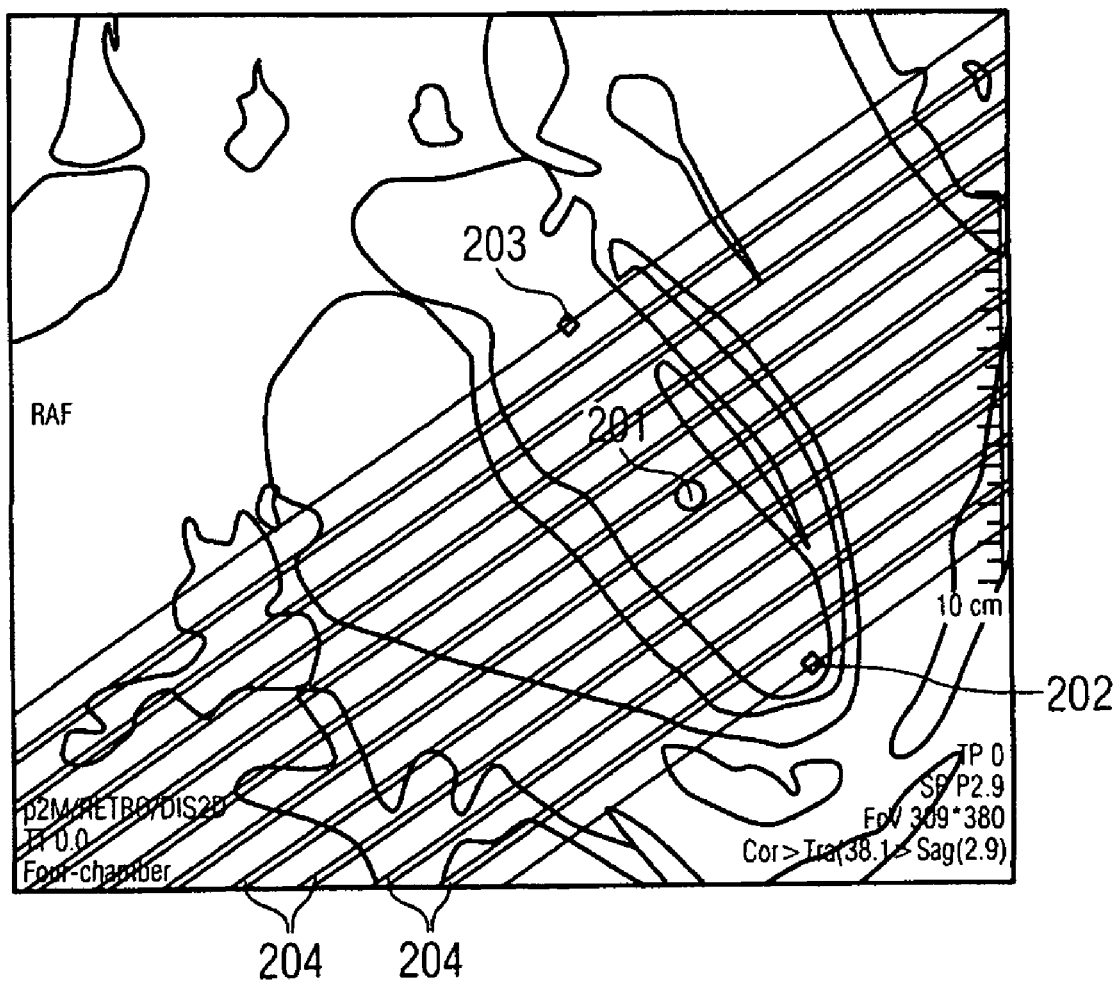

FIG. 2 shows a 4-chamber view of a heart, in which the recording of magnetic resonance data is planned.

Figure 3:
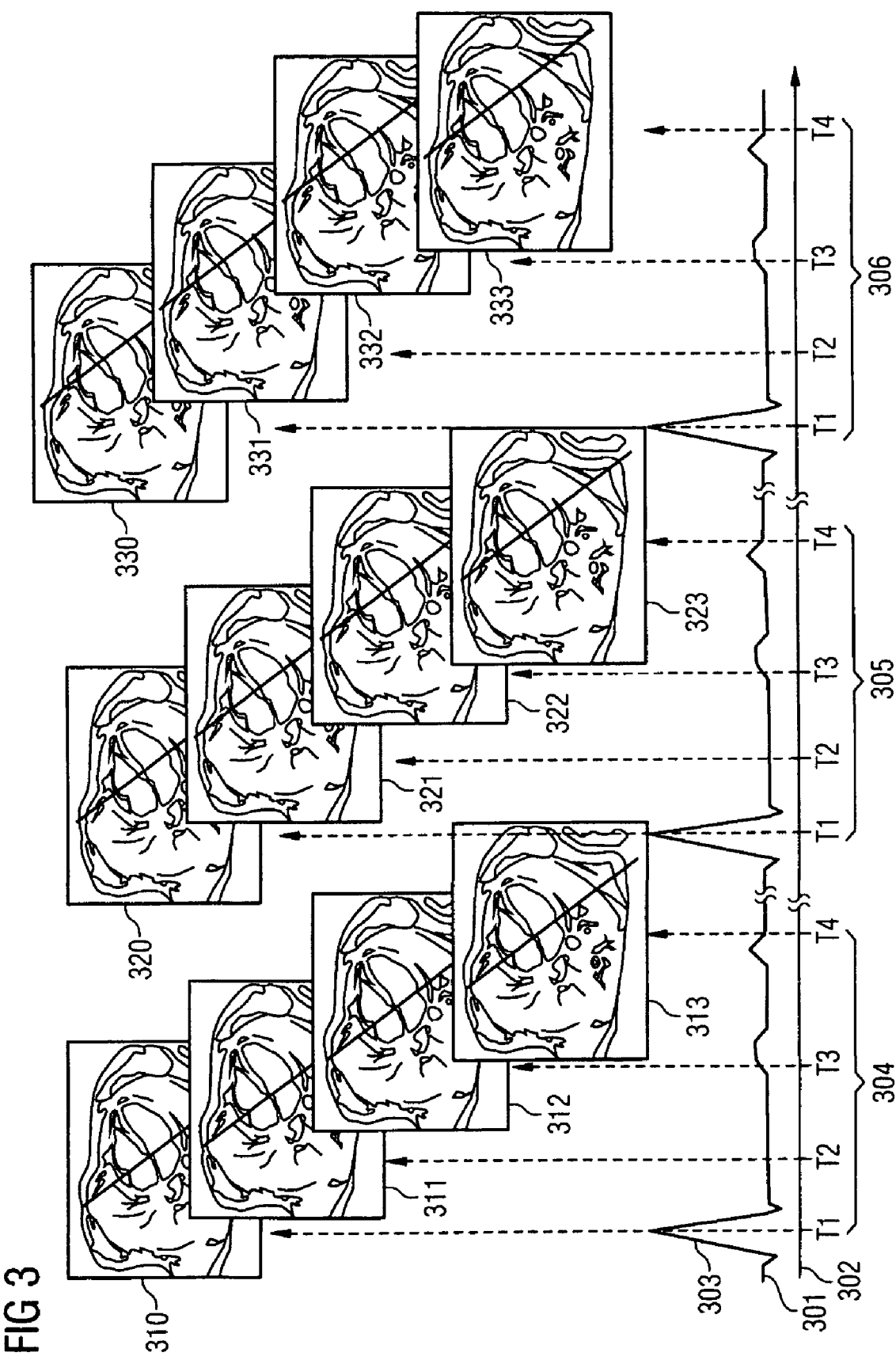

FIG. 3 is a schematic representation of ECG-triggered recording of layer images by a magnetic resonance apparatus.

Figure 4:
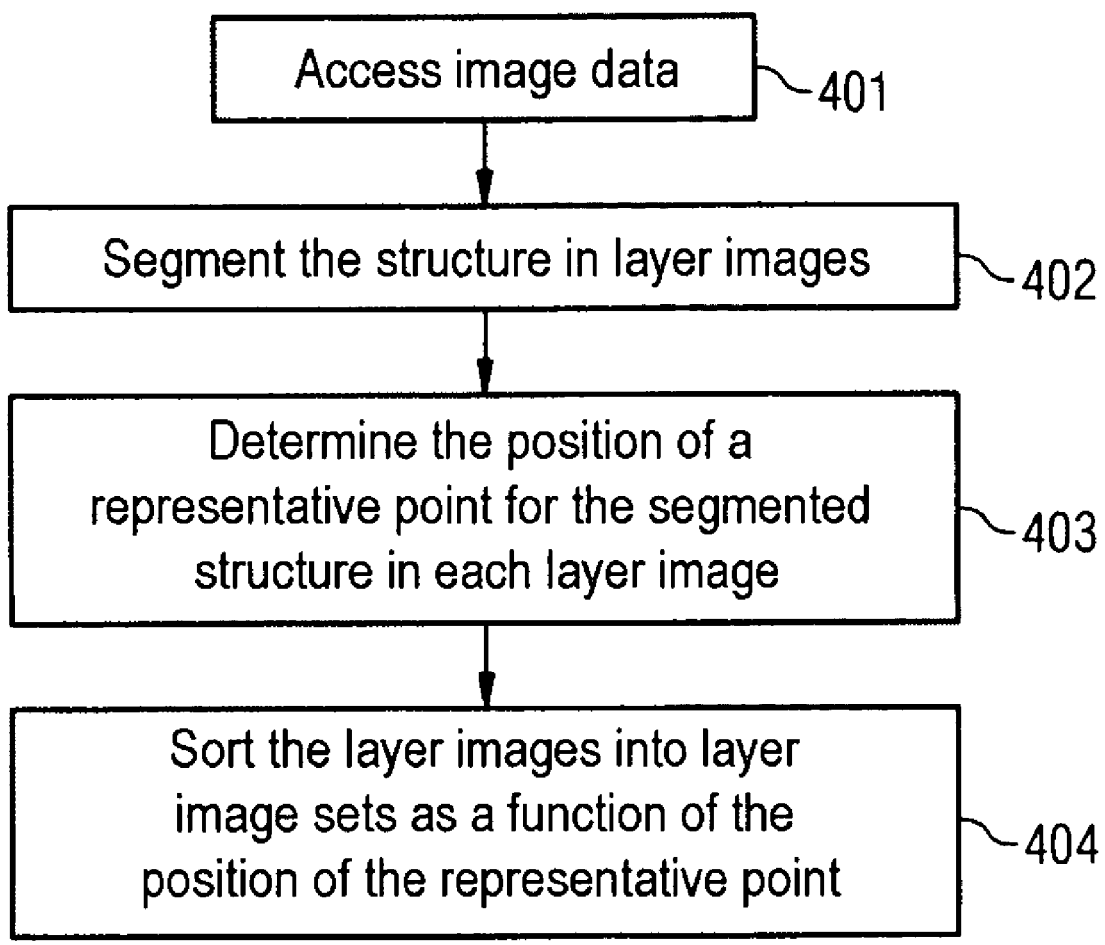

FIG. 4 shows a flow chart of an embodiment of the method according to the invention.

FIG. 5 is a schematic representation of the segmentation of a structure in a layer image.

Figure 6:
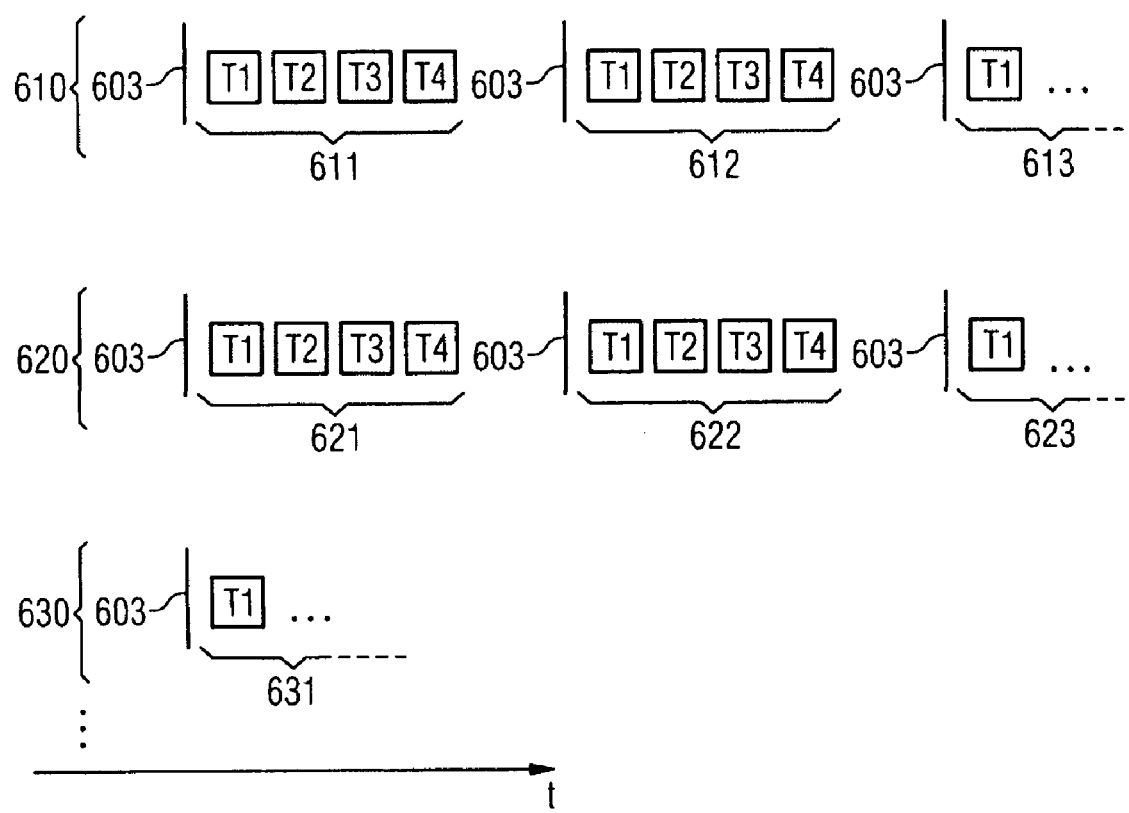

FIG. 6 is a schematic representation of the structure of image data, which have been recorded for various layers and following a number of trigger events.

Figure 7:
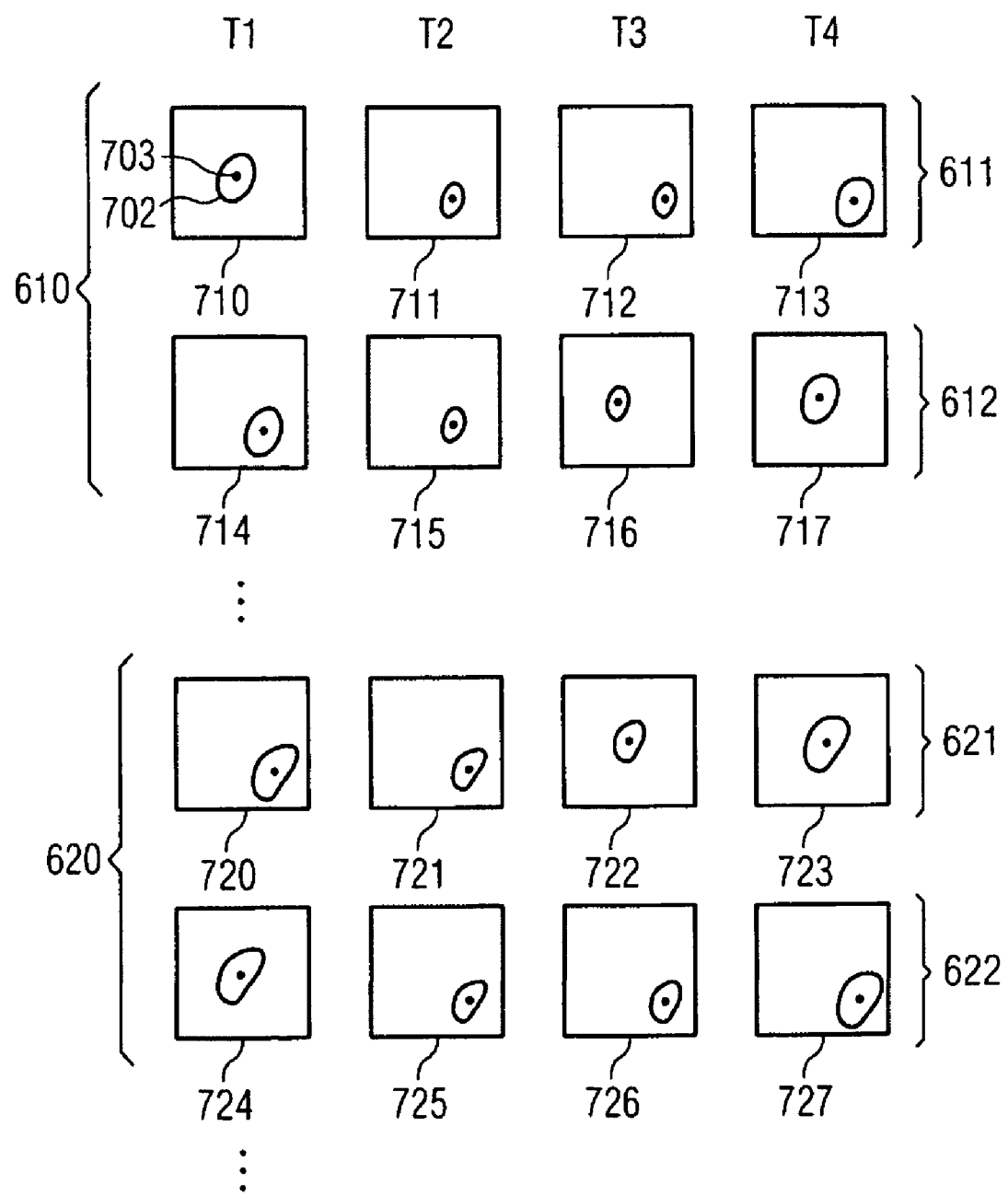

FIG. 7 shows a schematic representation of the structure of the image data after layer images have been ordered according to their time stamps.

Figure 8:
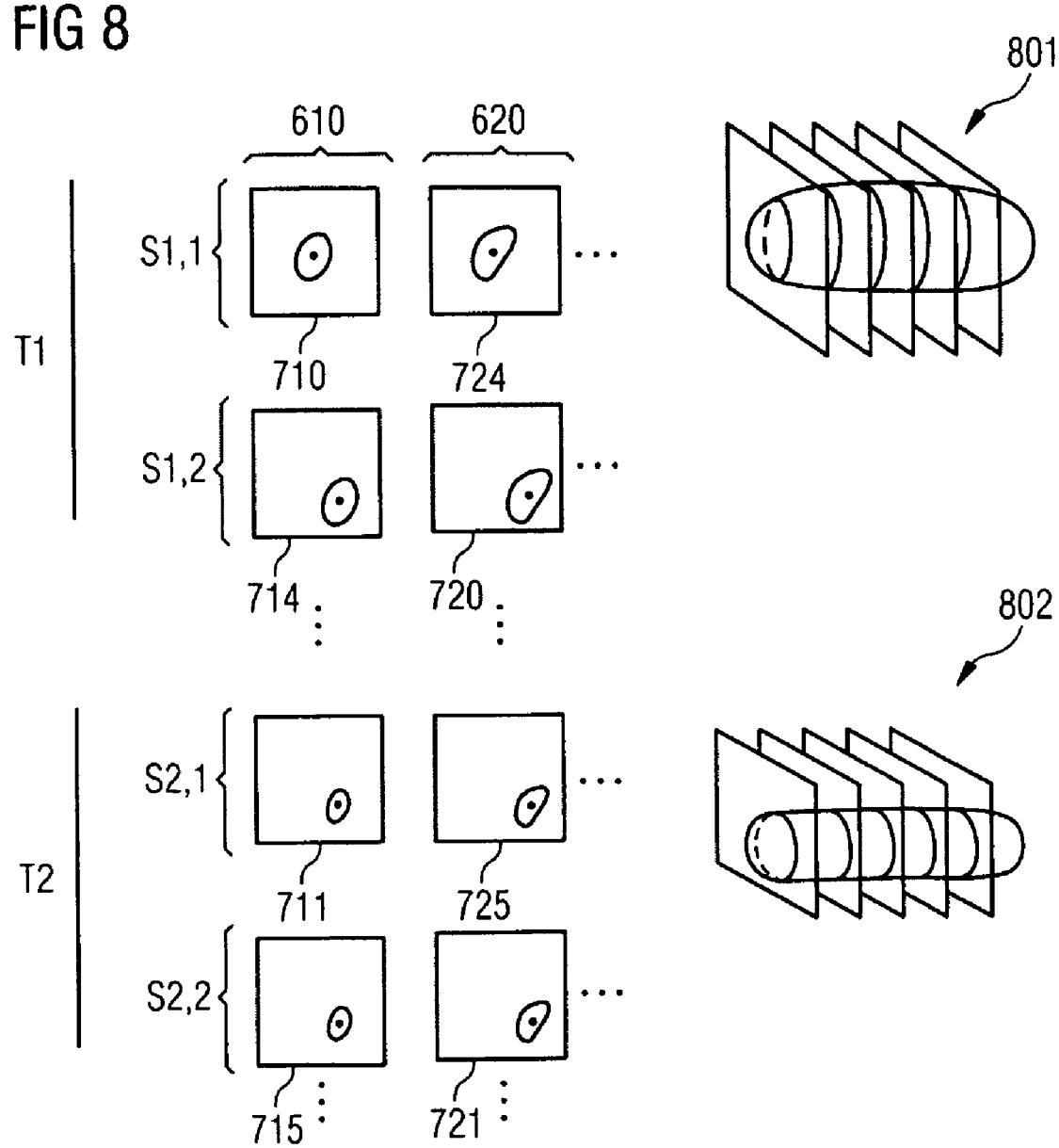

FIG. 8 shows a schematic representation of the layer images, which are contained in various layer image sets that correspond to different time stamps.

Figure 9:
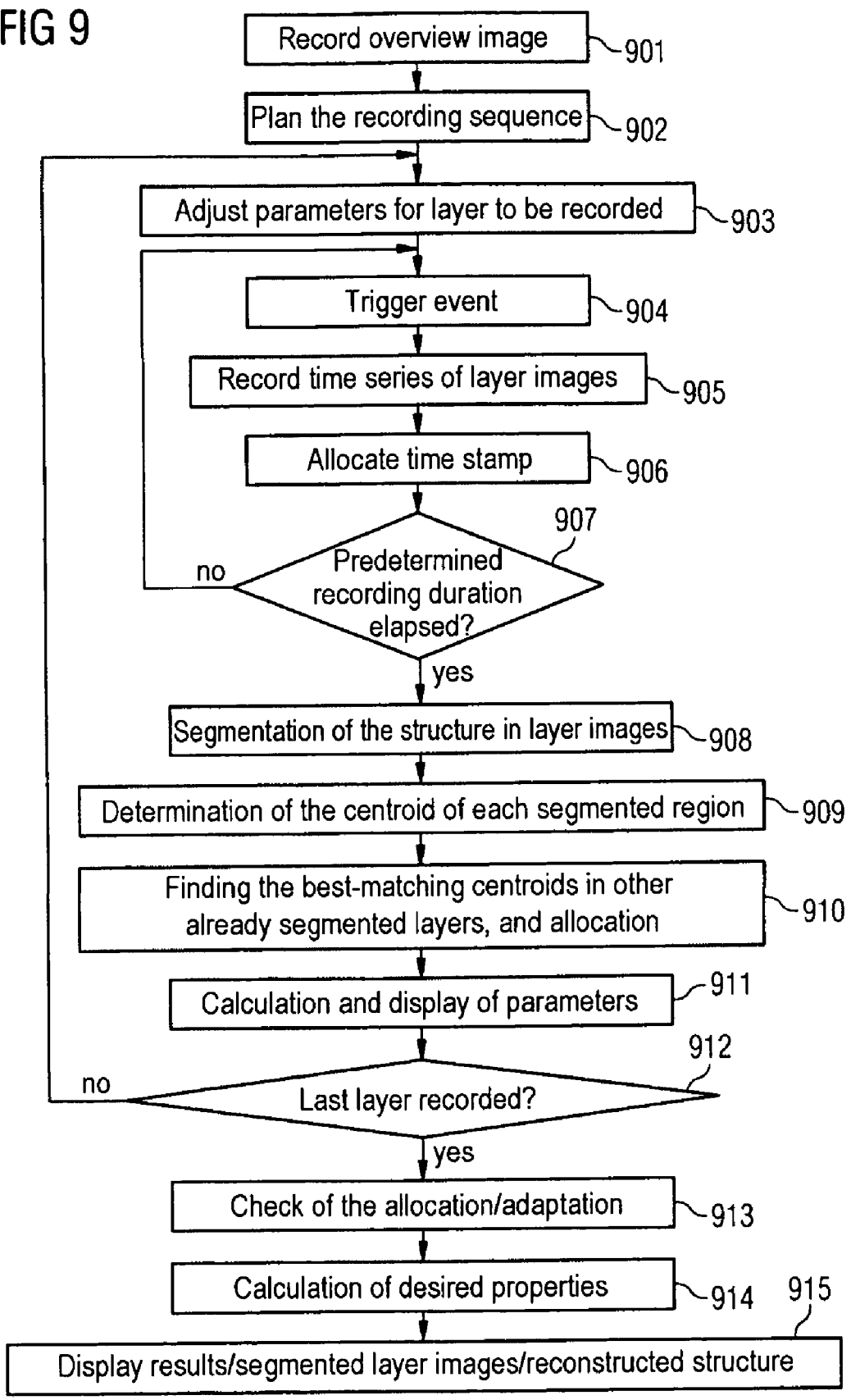

FIG. 9 shows a flow chart of another embodiment of the method according to the invention.

Figure 10:
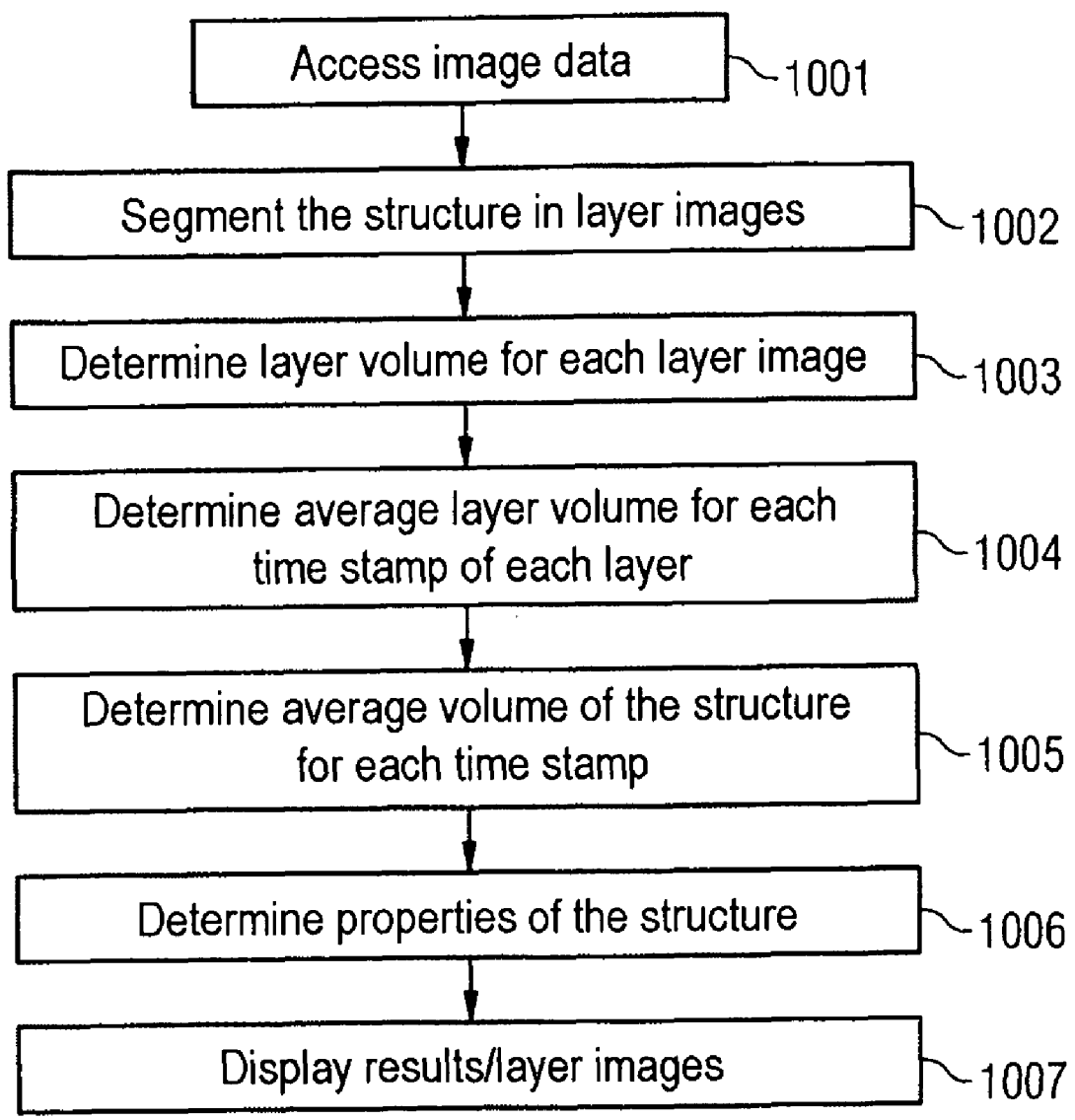

FIG. 10 shows a flow chart of an embodiment according to another aspect of the present invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 schematically shows a magnetic resonance apparatus, with which an image data set can be recorded from a subject's region to be examined. Such a magnetic resonance apparatus 100 has a magnet 101 for generating a polarization field $B_0$. An object to be examined, here a subject 102, is moved into the magnet on a table 103 as represented schematically by the arrows 104. The magnetic resonance apparatus furthermore has a gradient system 105 for generating magnetic field gradients, which are used for the imaging and position encoding.

In order to excite the polarization obtained in the primary field, a radiofrequency coil arrangement 106 is provided which radiates a radiofrequency field into the person 102 being examined, so as to displace the magnetization from the equilibrium position. A gradient unit 107 is provided for controlling the magnetic field gradients, and an RF unit 108 is provided for controlling the applied radiofrequency (RF) pulse. A control unit 109 centrally controls the magnetic resonance apparatus, and the imaging sequences can likewise be selected in the control unit 109. Via an input unit 110, an operator can select a sequence protocol, and enter and input and modify imaging parameters which are shown on a display 111.

The general functionality of a magnetic resonance apparatus is known to the person skilled in the art, and a more detailed description of the general components will therefore not be provided here. The magnetic resonance apparatus furthermore has a computer unit 112 in which, for example, recorded magnetic resonance signals can be reconstructed to generate image data. The computer unit 112 can furthermore be used to process such image data during or after the recording of magnetic resonance signals. Magnetic resonance signals from an examination region 113 are recorded with the aid of induction coils, which either are integrated in the RF system of the magnetic resonance apparatus or may be positioned as separate elements in the vicinity of the examination region.

By applying a layer selection gradient using the gradient system 105, for example, magnetic resonance signals from a layer can be recorded from the examination region 113, and a layer image can be reconstructed from the signals by the computer unit 112 and shown to a user of the magnetic resonance apparatus on the display 111. By applying various gradients, for example layer selection, phase encoding and frequency encoding gradients, it is possible to record magnetic resonance signals from which a multiplicity of different views of a structure of the object to be examined can be reconstructed.

A recording unit of the MR apparatus may for example comprise the gradient unit 107, the RF unit 108, the radiofrequency coil arrangement 106, the gradient system 105 and the magnet 101, as well as further induction coils (not shown).

The recording of magnetic resonance signals is initiated by a trigger unit 114. The initiation may for example be carried out by ECG triggering, which is indicated in FIG. 1 by an ECG electrode 115. When the trigger signal is detected, the trigger unit 114 enables the control unit 109 to start a predetermined imaging sequence. A plurality of such imaging sequences may be recorded for each layer. The recording is furthermore carried out over various layers, so that the image data for different layers respectively comprise a plurality of layer images.

FIG. 2 shows the way in which the recording of such an image data set can be planned. In particular, the recording of image data and the segmentation thereof will be described in the following examples with reference to the example of a subject's left ventricle. FIG. 2 shows a layer image of the subject's heart, this representation being a so-called 4-chamber view in which the four heart chambers are visible. The left ventricle 201 is represented here in a longitudinal section, i.e. its longitudinal axis lies in the plane of the image.

In order to record image data of the left ventricle, it is advantageous to record section images which are perpendicular to the ventricle's longitudinal axis, which extends from the apex 202 to the opening of the mitral heart valve 203. The 4-chamber view of FIG. 2 shows section planes 204, for each of which a layer image is intended to be recorded. The section planes 204 extend perpendicularly to the plane of the page, and for this reason they are indicated as lines. A layer image which is recorded from such a section plane will be referred to as a short-axial image, since a section through the ventricle is imaged therein in a plane in which the short axes or transverse axes of the ventricle lie.

Preferably, a plurality of layer images are recorded for each layer along this principal axis of the ventricle. It may generally be assumed that in any phase of the cardiac cycle, the centroid of a short-axial section through the left ventricle lies on this principal axis. The position and orientation of this principal axis may however vary during successive cardiac cycles, for example owing to breathing. Such a displacement of the position of the heart while image data are being recorded can, however, be compensated for by the method described below.

FIG. 3 schematically illustrates the way in which the recording of image data from various layers can be carried out. Preferably, image data for at least two breathing cycles of the subject are recorded for each layer. The image data are recorded by recording magnetic resonance signals and reconstructing layer images. FIG. 3 shows a trace of an electrocardiogram 301, which is plotted against a time axis 302. The ECG has R-wave peaks 303. First layer images 304 are recorded during a first time series in a first layer. The recording is triggered on the R-wave peak 303.

A time series comprises the layer images which have been recorded following a trigger event and before the occurrence of the next trigger event. For the first layer, further layer images (not shown) are recorded after the first layer images 304, which is indicated by the interruption of the ECG curve and the time axis. The first time series of the first layer comprises the layer images 310 to 313, which have been recorded at predetermined times with the time stamps T1 to T4. The time stamps T1 to T4 indicate the time interval of the recording of the layer image with respect to the trigger event. Second layer images 305 are recorded from a second layer.

The first time series of layer images from this second layer comprises the layer images 320 to 323. These layer images are recorded at the same relative times as the layer images 310 to 313. The layer images are therefore likewise allocated essentially the same time stamps T1 to T4. Owing to the hardware-related delays, accuracy of the values and the like, minor differences may occur between the time stamps of different time series or layers.

Differences of up to ±5 ms may occur between the time stamps. Typically, the difference is ±2.5 ms. The same procedure is adopted with the layer images which are recorded during a second time series from the same layer. After a group of time series have been recorded, preferably over two breathing cycles of the subject, operation continues with the next layer. Only one time series is likewise represented for the second layer in FIG. 3, which is again illustrated by the interrupted time axis and ECG curve.

Third layer images 306 are in turn recorded at relative times T1 to T4 following a trigger event 302. The first time series of the third layer comprises the layer images 330 to 333. For clarity, only four layer images are shown for a time series in FIG. 3. During a time series which extends over a cardiac cycle, however, images are recorded with an interval of preferably 60 ms. With a heartbeat frequency of 75 beats per minute, a time series therefore comprises approximately 13 layer images. Such recording of layer images may be referred to as realtime recording. The recording is preferably carried out over 10 seconds per layer, so that 12.5 time series are recorded for each layer. It should be clear that the values mentioned here only represent examples, and that other recording times or time intervals between recorded layer images may also be used. The layer images are allocated the time stamp, and also a time stamp which indicates a duration relative to the start of recording layer images from the corresponding layer.

FIG. 4 shows a flow chart of an embodiment of the method according to the invention. In a first step 401, image data are accessed. This may for example be done during recording of the image data, or after an image data set has been recorded. The image data are provided, for example, by the magnetic resonance apparatus 100. The image data image a structure of an object to be examined layer by layer, and they comprise a plurality of layer images for each layer. In a next step 402, the structure is segmented in layer images. A possible form of the segmentation of the structure in the layer images will be described below with reference to FIG. 5.

After step 402, for example, a plurality of layer images in which the structure has been segmented are available for each layer. Owing to the movement of the heart during the cardiac cycle and the movement of the thorax due to breathing, the position of the structure, which in this case is the left ventricle, may be displaced in the layer images. If all initially recorded layer images of each layer were then to be combined as a layer image set, then the positions of the structures in the individual layer images would not coincide since the layer images have been recorded for example in different phases of the breathing cycle. For this reason, in step 403, the position of a representative point is determined for the segmented structure in each layer image.

For example, the position of the centroid of the segmented structure in a layer image is determined on the basis of a segmentation region with the aid of numerical methods. Other points may nevertheless be selected as representative points, which are determined on the basis of other properties of the segmented regions. In a subsequent step 404, the layer images are sorted into layer image sets as a function of the position of the representative point. A layer image from each plane is respectively sorted into each layer image set. If equally many layer images are recorded for each plane, then the same number of layer image sets can be compiled. It is however also possible to compile fewer layer image sets, in which case layer images in which the position of the representative point differs from the positions of the representative points in the layer image sets may be discarded.

Various methods may be envisaged for selecting the layer images for a layer image set. The layer images may, for example, be selected so that their representative points lie essentially on a line. With reference to the example of the left ventricle, this is preferably the line which extends from the heart apex to the opening of the mitral heart valve. For such allocation of the layer images, for example, layer images for which the positions of the representative points in the plane lie as close as possible to one another may be selected for a data set. For each layer image set, it is thus possible to minimize the transverse spacings of the representative points. This may, for example, be done by an iterative search method. The allocation of layer images to layer image sets will be described in more detail below with reference to FIG. 8.

The compilation of layer image sets by an embodiment of the method described above may also be referred to as rigid image registering, since no transformations are applied to the layer images here; rather, the layer images essentially remain unmodified. A match of neighboring layer images is achieved by the allocation, or by the search method. The method of such an embodiment is therefore substantially less elaborate, as relates to the computing time and computing power.

FIG. 5 shows a schematic representation of the segmentation of a structure in a layer image. FIG. 5a shows a layer image 501, in which a section through a subject's thorax is imaged. The layer image 501 shows a section through the heart 502, as well as other structures 503.

The heart 502 has a left ventricle 504 and a right ventricle 505. In this example, the left ventricle 504 is the structure which is intended to be segmented.

Owing to the heartbeat, the imaging of the left ventricle varies in consecutive images of a time series. Such a time series of layer images is analyzed in order to locate the heart. For example, image subtraction and statistical analysis of the subtraction images are employed in order to generate a binary image, which indicates the positions of the predominant moving structures in the image.

FIG. 5b shows an example of a variance image in which structures, which experience variations as a function of time, are represented with high contrast relative to stationary structures. Such a variance image may for example be calculated from a time series of layer images by a method as described in W. Soergel and V. Vaerman, SPIE: Med. Imag. 1997; 3034; 333-344, the entire contents of which are hereby incorporated herein by reference. By using a threshold value, such an image can be converted into a binary image. Threshold value methods are widely known; for example, image pixels may be set to the values 0 or 1 depending on whether their intensity lies above or below the threshold value.

The variance image 506 shows the heart 502 before application of a threshold value method. If other varying structures are imaged in the layer images of the time series, then these structures may also be present in the variance image 506.

After conversion of the variance image 506 into a binary image, a left ventricle is subsequently identified in the binary image. Such identification is possible for example on the basis of the roundness, the connection and the position of structures in the binary image. The left ventricle can generally be identified as a round object, which lies in the vicinity of the image center. It is therefore possible to distinguish the left ventricle from other structures which are imaged in the binary image.

FIG. 5c shows such a binary image, in which the left ventricle 504 has been identified as an initial structure 510. In order to distinguish the heart from other structures imaged in a binary image, a mask may furthermore be compiled in which for example binary images from a plurality of layers are analyzed, in which case the heart can essentially be identified as the structure which is imaged in all the layers. Such an optional extra step is expedient when image data from a plurality of layers are already available. With such a mask, structures which do not belong to the heart can then be filtered out in binary images.

In the binary image 507, which images the left ventricle 504, an initial contour 508 may subsequently be established. The initial contours may for example be established by using a heart model, or by using the contour from a neighboring layer, or a simple geometrical shape, for example a circle or an ellipse. The method described in M. P. Jolly, Proc. MICCAI, 2001 or in WO 2006/083588 A1, the entire contents of each of which are hereby incorporated herein by reference, is however preferably used to establish the initial contour. For example local maxima are identified in a histogram of the layer image, on the basis of which region-based segmentation of the layer image is carried out. Based on the result and gradients in the layer image, initial boundaries of the left ventricle are established.

On the basis of the initial contour or contours, the individual images of the time series are subsequently segmented. For each layer image, an initial contour is adapted to the edges of the left ventricle which are imaged in the layer image, by deformation. To this end an active contour method may be used, for example "Snakes", and it is preferable to use the method described in M. P. Jolly, Proc. MICCAI, 2001 or in WO 2006/083588 A1.

On the basis of the initial position determination of the left ventricle, for example in the binary image 507 in FIG. 5c, other methods may also be used for segmentation of the left ventricle, for example the "deformable shape model" method described in M. Kaus et al., "Automated segmentation of the left ventricle in cardiac MRI", Medical Image Analysis, 2004; 8:245-254, or the "gradient vector flow" method described in C. Xu and J. L. Prince, "Snakes, Shapes, and Gradient Vector Flow", IEEE Transactions on Image Processing, 1998; 7(3): 359-369, the entire contents of each of which are hereby incorporated herein by reference.

FIG. 5d shows the result of the adaptation of an initial contour by deformation. The adapted contour 509 adjoins the edge of the left ventricle 504 and defines a segmentation region. Adaptation of the contour to the wall of the ventricle 504 is made possible, for example, because the wall of the ventricle is imaged with contrast relative to the surrounding image points, so that there is a high gradient in the layer image in this region, on the basis of which adaptation of the initial contour can be carried out. For such adaptation, however, it is advantageous to introduce boundaries relating to the shape, so that the contour cannot deviate substantially from the shape of the left ventricle owing to the deformation. For a further improvement of the segmentation, the method described in M. P. Jolly, Proc. MICCAI, 2001, the entire contents of which are hereby incorporated herein by reference, may also be applied two times.

After each image of a time series has been segmented, a consistency check of neighboring layer images of the time series may furthermore be carried out. The imaged structure has only minor variations in directly neighboring layer images. The shape and the position of neighboring contours can therefore be compared and checked for consistency. If the deviations in shape and position exceed a predetermined value, a correction of the contours may be carried out. Such correction of the contours may for example be carried out by contour propagation or extension or contour adaptation, as described in WO 2006/083588 A1, the entire contents of which are hereby incorporated herein by reference. Such a procedure will improve the reliability of the segmentation. After all the images of all time series of a layer have been segmented, the contours may in turn be compared in order to ensure consistency in position and shape of the contours over the layer. If necessary, contour adaptation may again be carried out as described above. The segmentation and optional checking and adaptation are repeated for each of the various layers.

As an alternative the automatic rough position determination of the structure to be segmented, and the segmentation of the structure in individual layer images, are carried out only for the first time series of each layer. For the remaining time series of the respective layer, the contours are calculated by contour propagation or extension methods. The adaptation of the contours to the edges of the structure to be segmented may in this case be carried out by one of the methods described above. This reduces the computing outlay for the segmentation of all the layer images of a layer.

Owing to the heart movement and the breathing cycle, the procedure described above is particularly advantageous for segmentation of the structure since the position of the structure is determined automatically in each time series. Adaptation of the initial contour to the edge of the structure is furthermore carried out, so that accurate segmentation is ensured. The method of at least one embodiment is therefore particularly suitable for the segmentation of a structure in image data which have been recorded from a freely breathing subject.

The allocation of layer images to layer image sets will be described in more detail below with reference to FIGS. 6-8. FIG. 6 shows the structure of the image data. For a first layer 610, the image data comprise the time series 611, 612 and 613. Further time series may also be available, although they are not shown in FIG. 6. The time series respectively comprise layer images with the time stamps T1 to T4. Each time series has been recorded following a trigger event 603, which is for example the occurrence of an R-wave peak in an ECG. For a second layer 620, the image data likewise comprise time series 621, 622 and 623 which in turn respectively have layer images with time stamps T1 to T4. The image data may comprise a third layer 630 and any number of further layers, as well as any number of further time series for each layer. A time series may also comprise substantially more than four layer images.

In real-time recording of the image data for a layer, the image data may also be recorded continuously, in which case a trigger event is used to start the recording. Time stamps are then allocated to the layer images recorded for the layer, on the basis of the further trigger events. Owing to the continuous recording, layer images of various time series of a layer may also have different time stamps.

FIG. 7 shows for illustration the layer images of each layer, ordered according to their time stamps. The columns denoted by T1 contain all layer images which have the time stamp T1. The time stamp indicates the time interval of the recording of the layer image relative to the preceding trigger event. It will again be assumed below that the left ventricle of a subject's heart is being segmented, and that the recording is triggered on the R-wave peak of an ECG.

Each of the columns shown in FIG. 7 therefore contains layer images which have been recorded from the same phase of the cardiac cycle. For subsequent compilation of a layer image set, it is expedient to select only layer images with the same time stamp since the heart has a different volume in different phases and meaningful volume calculation would not therefore be possible with mixed time stamps. Two time series 611 and 612 are in turn shown for the first layer 610, which contain the layer images 710 to 713 and 714 to 717, respectively. In the first layer image 710 of the first time series 611, the segmented structure 702 is represented in the form of a contour as well as a representative point 703, which has been determined for the segmented structure 702.

In the further layer images 711 to 717 and 720 to 727 in FIG. 7, the structure segmented in these images and a representative point determined for the segmented structure are likewise represented, although for the sake of clarity these are not provided with references. In general, a time series corresponds to a cardiac cycle. For this reason, the area of the segmented ventricle changes in the layer images 710 to 713 of the first time series.

The cycle of the exemplary representation of FIGS. 7 and 8 shows first the contraction phase of the heart (volume decrease) and subsequently the relaxation phase (volume increase). For example, the area decreases in layer images 711 and 712 owing to the reduction of the ventricular volume, whereupon the area is increased again in layer image 713. A position displacement of the segmented structure furthermore takes place in the layer images of the first time series 611, which is caused for example by the breathing of the subject. Since the breathing cycle and cardiac cycle are repeated with different frequencies, the segmented structure is located at different positions in layer images with the same time stamp. For example, the segmented structure has the same area in layer images 712 and 714 but is displaced in its position.

The same can be observed in the layer images of the first time series 621 and the second time series 622 of the second layer 620. In particular, the positions of the structure in the first time series of the second layer do not coincide with the positions of the structure in the first time series of the first layer, so that simple allocation of the layer images to layer image sets is not possible. Yet, since a plurality of layer images are available for each time stamp for each layer, it is possible to sort the layer images so that the position of the segmented structure essentially coincides in layer images which are allocated to one another. Such allocation or sorting is carried out on the basis of the representative point 703.

With the aid of the representative point, simple and rapid allocation of the layer images to layer image sets is possible. For example, the position of the representative point in each layer image is determined as an X/Y pixel position. Layer image sets are subsequently formed from one or more layer images of the first time stamp of the first layer, and layer images with the time stamp T1 of the second layer are then allocated to them so that the spacings of the X/Y pixel positions of the representative points in the layer images of a layer image set are as small as possible. For example, the layer image 720 of the second layer 620 is allocated to the layer image set which contains the layer image 714 of the first layer 610, since the representative point in layer image 714 lies closer to that in layer image 720 than the representative point in layer image 710 does. The spacings of the representative points in the layer image plane are thus minimized. For each image data set for example, the allocation may be carried out by an iterative sorting method which minimizes the transverse spacings of the representative points in each layer image set.

As an alternative, however, a region could also be established around each representative point, layer images being assigned to a layer image set if their representative point lies in the region of a layer image already allocated to the layer image set. The first allocated layer image could for example be used as a reference image, subsequent layer images being allocated on the basis of the representative point of this reference image. As an alternative, the allocation could however also be carried out on the basis of the layer images from neighboring layers. This is advantageous in particular when the allocation is already being carried out while layer images are recorded. Since the layers are recorded consecutively, spatially coinciding representative points may already be found while each layer is being recorded, and the allocation may be refined continuously until the last layer has been recorded.

FIG. 8 shows an exemplary allocation of the layer images of FIG. 7 to layer image sets. In FIG. 8, two layer image sets S1,1 and S1,2 are compiled for a time stamp T1, and layer image sets S2,1 and S2,2 are compiled for a second time stamp T2. Layer image sets may naturally be compiled for more than two time stamps, and likewise more than two layer image sets may be compiled for each time stamp. Each layer image set preferably contains one layer image from each layer. For the sake of clarity only layer images from two layers 610 and 620 are shown for each layer image set in FIG. 8. For the time stamp T1, a first layer image set S1,1 and a second layer image set S1,2 have respectively been compiled on the basis of the layer images 710 and 714 from the first layer 610.

The layer image 724 from the second layer has been allocated to the first layer image set S1,1, since the distance between the representative points in the plane of the layer images 710 and 724 is less than the distance between the representative points from the layer images 710 and 720. Layer image 720 has likewise been allocated to the layer image set S1,2 on the basis of the position of the representative point. The layer images with the time stamp T2 are allocated similarly to the layer image sets S2,1, S2,2, etc. Preferably, at least one layer image set is compiled for each time stamp. In this way, various layer image sets are obtained in which the positions of the segmentation regions of the structure match in the layer images. From such a layer image set, volume determination of the structure can consequently be carried out for a phase of the cardiac cycle indicated by the time stamp, as well as three-dimensional reconstruction of the segmented structure.

A schematic representation of such a reconstruction is shown in FIG. 8 for the layer image sets S1,1 with the time stamp T1 and S2,1 with the time stamp T2. Owing to a volume change of the structure between the relative times T1 and T2, the reconstructed structure 801 has a larger volume than the reconstructed structure 802. If a plurality of layer image sets are compiled for a time stamp, then the user can select a suitable layer image set for subsequent evaluation, for example the layer image set in which the distances between representative points of the layer images are minimal. With such sorting of the layer images according to their representative points, however, it is possible that a particular layer images will not be assigned to a layer image set if for example the position of the representative point differs significantly from that of the other layer images in the layer image sets. Such incompatible layer images may, for example, be stored separately or discarded. Accordingly, it is advantageous not to compile a layer image set for each time series which has been recorded for a layer.

The allocation may also be carried out according to time series, for example by using only the representative points of the first image of each time series for the allocation. In this case a time series is selected for each layer, and the layer images with equal time stamps in the selected multiple time series respectively form a layer image set.

In the layer image sets which have been compiled for a time stamp, the segmented structure may be located in different positions. These different positions are caused, for example, by the breathing cycle of the subject. By selecting a particular layer data set, it is therefore possible to select segmentation of the structure which corresponds to a particular phase of the breathing cycle. With the described method of at least one embodiment, it is therefore likewise possible to obtain information about variations of the structure in the course of the breathing cycle.

When a sufficient number of time series are recorded per layer, for example 10-20, it is usually possible to compile image data sets in which the representative points of the various layer images essentially coincide. Recording a large number of layer images for each layer is therefore advantageous for the compilation of the layer image sets. Despite the fact that the subject breathes freely while the image data are being recorded, with the described method it is possible to segment the structure in three dimensions and perform a volume calculation.

Compared with conventional methods, no changes or transformations of the layer images are necessary. It is also not necessary to record the image data by using breath triggering. The segmentation and allocation of the layer images to the layer image sets can be carried out fully automatically. Further advantages are the speed of the method of at least one embodiment and low requirements for the computing power.

After the layer image sets have been compiled, they may for example be stored on a data medium. The layer image sets may subsequently be processed for evaluation. As an alternative, evaluation may also already be carried out during the allocation of the layer images to the layer image sets, for example by calculating a layer volume of the structure segmented in the layer image.

FIG. 9 shows a flow chart of an alternative embodiment of the method according to the invention. In a first step 901, an overview image of a region to be examined in the subject is recorded. To this end, for example, the subject is positioned in the magnetic resonance apparatus and connected to necessary trigger and monitoring instruments. Image data are subsequently recorded in order to locate the heart in the subject's thorax. For example, a 4-chamber view of the heart may be recorded as an overview image. This may also be done with real-time imaging or "CINE" MRT imaging.

In a next step 902, a recording sequence for the image data is planned on the basis of the 4-chamber view. For example, the recording of a predetermined number of short-axial layer images is planned, i.e. layer images which image the short axes of the left ventricle, as a stack of parallel sections in the 4-chamber view. As may be seen in FIG. 2, the stack preferably extends from the mitral heart valve to the heart apex.

In a next step 903, parameters are adjusted for recording layer images from the first layer. The adjustment is preferably carried out by the magnetic resonance apparatus on the basis of the planning referred to in step 902. Layer images of the layer are now recorded over a predetermined duration. First, a trigger event occurs in step 904; for example, the occurrence of an R-wave peak in the ECG is established. This is followed by the recording of a time series of layer images in step 905, the layer images preferably having a predetermined time interval from one another, for example 60 ms.

In step 906, the layer images are respectively allocated a time stamp which indicates their recording times relative to the trigger event. If the predetermined recording duration has not yet elapsed in the decision 907, a further time series of layer images is in turn recorded in step 905 following a subsequent trigger event in step 904. This is done until the predetermined recording duration has elapsed, whereupon the structure imaged in the layer images is segmented in step 908. As an alternative, the layer images of the multiple time series may be recorded continuously following the trigger event 904. The trigger events are then used only to establish the time stamps. In this way, the recording is thus triggered only once for each layer.

After the structure has been segmented in the layer images, the centroid of the segmented region in each layer image is determined in step 909. The geometrical centroid of the segmented region may be determined by conventional methods, which will not be discussed in further detail here. In a next step 910, the layer images are allocated to layer image sets. In general, the allocation is carried out by finding the best-matching centroids in other already segmented layers in the layer image sets.

When recording the first layer, however, the layer image sets are compiled for a predetermined number of layer images, at least one layer image set being compiled for each time stamp. For example, layer image sets in which the representative point lies as close as possible to the center of the layer image are compiled for the layer image sets. The representative points of these initially assigned layer images then form the basis for the further allocation of the layer images from the other layers.

In a next step 911, parameters are calculated and displayed. For example, a volume of the segmented structure may be determined for the layer, or a volume change of the structure in the layer, or the cumulative volume of the layer images already allocated to a layer image set. The layer images themselves, or partial reconstructions of the structure to be segmented, may furthermore be shown on a display. Displaying the segmented regions in the layer images, for example, can make it possible for a user of the magnetic resonance apparatus to check the quality of the segmentation visually. An estimate of the ejection fraction of the left ventricle may also already be calculated, and displayed to the user together with the segmented layer images. This estimate may be improved continuously with the recording of layer images from further layers.

The decision 912 checks whether the last layer has been recorded. If this is not the case, the method continues with step 903 in which the parameters for recording the next layer are adjusted, preferably automatically, by the magnetic resonance apparatus. In the steps 904 to 907, a plurality of time series of layer images are again recorded. After the segmentation of the structure in step 908 and determination of the centroid of each segmented region in step 909, the layer images are assigned to the layer image sets in step 910. The allocation is now carried out by comparing the centroids determined in the layer images in the first layer image sets with the centroids of the recorded layer images, and assigning these to the corresponding layer image sets. This procedure is repeated until it is found in step 912 that the last layer has been recorded. As an alternative, the recording of the next layer by steps 903 to 907 may also be carried out already while processing the layer images of the last layer 908 to 911. In this way, a further time saving is achieved.

A check of the allocation of the layer images to layer image sets is carried out in step 913, and optionally adjustment. A match of the segmented regions in the layer image sets can thereby be improved further. Such checking and adaptation of the allocation may also be carried out already while recording the further layers, so that the allocation is improved continuously. In step 914, desired properties of the structure to be segmented are calculated. These include for example the volume of the structure, volume changes of the structure which may be obtained for example as a function of the relative time interval from the trigger event, and similar properties, in the case of the left ventricle for example an amount of blood ejected or an analysis of the ventricular movement.

It is of course also possible to calculate other properties or parameters of the segmented structure, which will not be mentioned in detail here. Such comprehensive evaluation is made possible in particular because a large number of layer image sets can be generated by the described method, in which the structure is segmented for example in various phases of the cardiac cycle and/or the breathing cycle.

In step 915, the results of the evaluation are displayed together with segmented layer images or with a reconstruction of the segmented structure. The availability of layer image sets for different time stamps also makes it possible in particular to compile an animation of the segmented structure, which may for example illustrate a volume change of the structure. The calculation of the properties in step 914 may for example be carried out by a geometrical method, for example a rectangle method or a modified Simpson method. The volume of the structure may for example be quantified by dividing the structure into a plurality of sub-volumes and summing these sub-volumes, while taking into account the resolution of the layer images and the spacing between the layers.

FIG. 10 shows a flow chart of an embodiment according to another aspect of the present invention. Image data, which image a structure layer by layer, are accessed in a first step 1001. The structure is segmented in the layer images in step 1002. The segmentation may be carried out as described with reference to FIG. 5. In step 1003, a layer volume of the segmented structure is determined for each layer image. For example, the area of the segmented structure may be calculated by a numerical method.

On the basis of the calculated area and the height or layer thickness of the layer from which the respective layer image comes, the layer volume for the segmented structure can be determined. The image data may have the structure described above, in which a plurality of time series of layer images are available for each layer, each layer image being allocated a time stamp.

In step 1004, the layer volumes of layer images with the same time stamp are averaged in each layer. The same number of average layer volumes are therefore determined for each layer, the number corresponding to the number of time stamps. For each time stamp, an average volume of the structure is subsequently determined in step 1005 by summing the average layer volumes from each layer with the same time stamp. The evolution of the volume of the structure as a function of time is thereby determined, for example over a cardiac cycle.

From the time-dependent volumes determined in this way, properties of the structure can be determined in step 1006. Inter alia, the volume change of the structure as a function of time may thereby be determined in a straightforward way, and thus for example the amount of blood ejected by a ventricle. The results are subsequently displayed in step 1007 together with layer images and the structure segmented therein.

Similarly as the method shown in FIG. 9, the method of FIG. 10 may also be carried out during recording of image data by a magnetic resonance apparatus. The determination of layer volumes or average layer volumes in steps 1003 and 1004 may, for example, be carried out while recording layer images of a layer. Likewise, layer images and the segmentation regions determined for each layer image may be shown on a display directly after segmentation has been carried out, or at a later time.

The method described with reference to FIG. 10 allows rapid and uncomplicated processing of the recorded image data. Modification or transformation of the layer images, as for example in the case of image registering, is not necessary. The method is therefore substantially more rapid and less computer-intensive than conventional methods of volume determination. By averaging layer volumes with the same time stamps, a high accuracy is furthermore achieved even if the image data have been recorded from a freely breathing subject.

The methods described with reference to the figures are merely example embodiments of the invention, and it should be clear that the invention is not restricted to them. The features described with reference to various embodiments may also be combined. For example, the determination of layer volumes and average layer volumes as described in FIG. 10 may be carried out simultaneously with or following the allocation of layer images to layer image sets as described with reference to FIGS. 4 and 9.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for processing medical image data which image a structure layer by layer, the image data for at least some layers respectively including a plurality of layer images, the method comprising:
    segmenting, by a computer unit, the structure in the layer images;
    determining, by the computer unit, a position of a point in one of the layer images, the point being representative of the structure segmented in the layer image, respectively for a plurality of the layer images in which the structure has been segmented; and
    compiling, by the computer unit, at least one layer image set by allocating a layer image to the layer image set, respectively, for the plurality of the layer images, the allocating being carried out on a basis of the determined positions of the representative points in the respective layer images.

2. The method as claimed in claim 1, wherein the allocating is carried out so that transverse spacings of the representative points of the layer images of the layer image set are minimized.

3. The method as claimed in claim 1, wherein at least two layer image sets are compiled and wherein the layer images are allocated to the layer image sets so that transverse spacings of the representative points of the layer images in the individual layer image sets are minimized.

4. The method as claimed in claim 1, wherein the allocation of a layer image to the layer image set is carried out on the basis of the position of the representative point in the layer image and the position of the representative point in the a layer image from a neighboring layer.

5. The method as claimed in claim 1, wherein the allocating of layer images to a plurality of layer image sets is carried out by iterative sorting, which allocates the layer images to the layer image sets so that the spacings of the representative points in each layer image set are minimized.

6. The method as claimed in claim 1, wherein the medical image data are recorded from a subject before or during processing, while the subject is breathing freely.

7. The method as claimed in claim 1, wherein each layer image is allocated a time stamp which indicates the recording time of the layer image relative to a preceding trigger event.

8. The method as claimed in claim 7, wherein a layer image set is only allocated layer images which have essentially the same time stamp.

9. The method as claimed in claim 7, wherein at least one layer image set is compiled for each time stamp.

10. The method as claimed in claim 7, wherein the occurrence of the trigger event is determined by using at least one of a vector cardiogram, an electrocardiogram and a pulse trigger device.

11. The method as claimed in claim 1, wherein the image data comprise at least two time series of layer images for each layer, each time series having been recorded following a trigger event.

12. The method as claimed in claim 11, wherein the layer images of a time series have a time interval of between 20 and 100 ms, and wherein the image data for each layer comprise consecutive time series of layer images which extend over a duration of at least two breathing cycles of a subject from which the image data have been recorded.

13. The method as claimed in claim 11, wherein a time series is selected for each layer on a basis of the representative point of a layer image of the time series, and wherein chronologically successive layer image sets are respectively formed from a layer image of the time series selected for each layer.

14. The method as claimed in claim 1, wherein the allocating of the layer images to the layer image sets is carried out during recording of the image data.

15. The method as claimed in claim 1, wherein the segmenting of the structure in a layer image comprises calculation of a contour around the structure with an active contour method.

16. The method as claimed in claim 1, wherein the segmenting of the structure in a layer image comprises determination of an initial segmentation region of the structure in the layer image on the basis of variations of the structure in chronologically successive layer images.

17. The method as claimed in claim 16, wherein the determining of the initial segmentation region comprises the use of a first threshold value for compiling a binary image with imaged structures based on a variance image and identification of the initial segmentation region on the basis of at least one of shape, connection and position of the imaged structures.

18. The method as claimed in claim 16, wherein the segmenting of the structure in a layer image comprises the determination of an initial contour on the basis of the initial segmentation region.

19. The method as claimed in claim 18, wherein the initial contour for segmenting of the structure is adapted to the edges of the structure in the layer image with an active contour method.

20. The method as claimed in claim 19, wherein the image data comprise at least two time series of layer images for each layer, the structure in the layer images of the first time series being segmented by adapting the initial contours to the edges of the structure in the layer images, and wherein the structure in the layer images of the at least one further time series is segmented by adapting the contours of the first time series to the structure in the layer images of the second time series.

21. The method as claimed in claim 1, wherein the segmenting of the structure in the layer images comprises a check for differences in position and shape of contours in neighboring layer images of a time sequence, adapting of the contours being carried out when it is found that the differences exceed a limit value.

22. The method as claimed in claim 1, wherein the position of a representative point in a layer image is determined on the basis of the shape and the position of the segmented structure in the layer image.

23. The method as claimed in claim 1, wherein the representative point in a layer image is the centroid of the structure segmented in the layer image.

24. The method as claimed in claim 1, wherein parameters, which relate to the function of the structure, are determined on the basis of the structure segmented in the at least one layer image set.

25. The method as claimed in claim 1, wherein the structure is a left ventricle of a subject.

26. The method as claimed in claim 25, wherein at least one of a volume of the left ventricle, an ejection fraction and a blood volume ejected by the left ventricle are determined on a basis of the left ventricle segmented in the at least one layer image set.

27. The method as claimed in claim 1, wherein an area of the segmented structure in a layer image or the volume of the segmented structure is determined by using at least one of a Simpson method, a rectangle method and a numerical integration method.

28. The method as claimed in claim 1, wherein the volume of the structure is calculated for at least one layer image set by calculating, for each layer image, a layer volume of the segmented structure in the corresponding layer on the basis of a layer thickness and the area of the segmented structure in the layer image, and by adding the layer volumes of the segmented structure of the layer images of the layer image set.

29. The method of claim 1, wherein the segmenting, determining and compiling are performed by a computer unit of a magnetic resonance apparatus.

30. A method for processing medical image data which image a structure layer by layer, the image data for at least some layers respectively comprising a plurality of layer images, the method comprising:
 segmenting, by a computer unit the structure in the layer images to ascertain a segmentation region;
 determining, by the computer unit, a layer volume of the structure for each of a plurality of layer images in which the structure has been segmented, on a basis of a respective segmentation region and a layer thickness;
 calculating, by the computer unit, at least one average layer volume of the structure, for each layer in which the structure has been segmented, by averaging layer volumes of layer images from the layer; and
 determining, by the computer unit, at least one average volume of the structure by summing a layer volume of the structure, respectively, from each layer in which the structure has been segmented.

31. The method as claimed in claim 30, wherein the structure is segmented by a method wherein the segmenting of the structure in a layer image comprises calculation of a contour around the structure with an active contour method.

32. The method as claimed in claim 30, wherein each layer image is allocated a time stamp which indicates the recording time of the layer image relative to a preceding trigger event, and wherein a plurality of average layer volumes of the structure are determined for each layer by respectively averaging the layer volumes, which are based on layer images from the layer with an equal time stamp, for different time stamps.

33. The method as claimed in claim 32, wherein an average volume of the layer is respectively determined for different time stamps, the average volume for a time stamp being determined by summing an average layer volume from each layer, which has been determined for the corresponding time stamp.

34. The method as claimed in claim 33, wherein the structure is a left ventricle, and wherein an ejection fraction or a blood volume ejected by the ventricle is determined from the average volumes of the left ventricle for different time stamps.

35. The method of claim 30, wherein the segmenting, determining and compiling are performed by a computer unit of a magnetic resonance apparatus.

36. A magnetic resonance apparatus for recording and processing medical image data, comprising:
 a recording unit to record magnetic resonance data sets; and
 a computer unit to, from a recorded magnetic resonance data set, reconstruct image data which image a structure layer by layer, the image data for at least some layers respectively comprising a plurality of layer images, the computer unit being configured to carry out the following,
  segmentation of the structure in the layer images,
  determination, respectively, of a position of a point in one of the layer images, the point being representative of the structure segmented in the layer image, respectively for a plurality of the layer images in which the structure has been segmented, and
  compilation of at least one layer image set by allocating a layer image to the layer image set respectively, for a plurality of the layer images, the allocation being carried out based upon the determined positions of the representative points in the respective layer images.

37. A computer program product having a computer program which carries out the following steps when it is run in a computer unit of a magnetic resonance apparatus:
 segmenting a structure in layer images which are comprised in medical image data, the medical image data formed from the structure layer recorded by layer by a recording unit of the magnetic resonance apparatus and respectively comprising a plurality of layer images for at least some layers;
 determining a position of a point in one of the layer images, the point being representative of the structure segmented in the layer image, respectively for a plurality of the layer images in which the structure has been segmented; and
 compiling at least one layer image set by allocating a layer image to the layer image set, respectively, for a plurality of the layer images, the allocating being carried out on a basis of the determined positions of the representative points in the respective layer images.

38. An electronically readable data medium having, stored thereon, electronically readable control information which is configured so that to carry out, when the electronically readable data medium is used in a computer unit of a magnetic resonance apparatus, the following:
 segmenting a structure in layer images which are comprised in medical image data, the medical image data formed from the structure layer recorded by layer by a recording unit of the magnetic resonance apparatus and respectively comprising a plurality of layer images for at least some layers;

determining a position of a point in one of the layer images, the point being representative of the structure segmented in the layer image, respectively for a plurality of the layer images in which the structure has been segmented; and compiling at least one layer image set by allocating a layer image to the layer image set, respectively, for a plurality of the layer images, the allocating being carried out on a basis of the determined positions of the representative points in the respective layer images.

* * * * *